United States Patent
Zhang et al.

(10) Patent No.: US 10,953,208 B2
(45) Date of Patent: Mar. 23, 2021

(54) TRIGGERABLE SHAPE MEMORY INDUCTION DEVICES

(71) Applicant: Massachusetts Institute of Technology, Cambridge, MA (US)

(72) Inventors: Shiyi Zhang, Brookline, MA (US); Yida Zhao, Urbana, IL (US); Carlo Giovanni Traverso, Etobicoke (CA); Robert S. Langer, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 1350 days.

(21) Appl. No.: 15/143,230

(22) Filed: Apr. 29, 2016

(65) Prior Publication Data
US 2016/0317796 A1    Nov. 3, 2016

Related U.S. Application Data
(60) Provisional application No. 62/156,000, filed on May 1, 2015.

(51) Int. Cl.
*A61M 37/00* (2006.01)
*A61L 31/06* (2006.01)
(Continued)

(52) U.S. Cl.
CPC ............. *A61M 37/00* (2013.01); *A61L 27/26* (2013.01); *A61L 27/446* (2013.01); *A61L 27/50* (2013.01);
(Continued)

(58) Field of Classification Search
CPC ........ A61L 27/50; A61L 31/041; A61L 31/06; A61L 31/128; A61L 31/14; A61L 2400/16; A61M 2205/0266
See application file for complete search history.

(56) References Cited

U.S. PATENT DOCUMENTS
3,844,285 A    10/1974   Laby
3,976,764 A     8/1976   Watanabe et al.
(Continued)

FOREIGN PATENT DOCUMENTS
CN    1805718 A    7/2006
CN    101511305 A   8/2009
(Continued)

OTHER PUBLICATIONS
International Search Report and Written Opinion dated Jul. 21, 2016 for PCT/US2016/030020.
(Continued)

*Primary Examiner* — Tiffany Legette
(74) *Attorney, Agent, or Firm* — Wolf, Greenfield & Sacks, P.C.

(57) ABSTRACT

In accordance with the invention, compositions, devices, and related methods have been developed for medical-related and other applications. In some embodiments, the devices and compositions described herein comprise a triggerable shape memory polymer network. In certain embodiments, the polymer network comprises a covalently cross-linked polymeric material and a non-crosslinked polymeric material associated with the crosslinked polymeric material. In some cases, the polymer network has a first configuration (e.g., as polymerized), and a second configuration (e.g., upon heating and deformation), such that the polymer network can be triggered to recover the first configuration upon heating the polymeric material above a softening temperature of the polymeric material. In certain embodiments, the polymer network comprises a plurality of particles capable of increasing the temperature of the polymer network (e.g., above the softening temperature) in the presence of an external stimulus such as induction, radio frequency, or magnetic resonance, such that the polymer network changes (Continued)

configuration. The polymeric material may be molded into any suitable shape.

19 Claims, 22 Drawing Sheets

(51) Int. Cl.
*A61L 27/50* (2006.01)
*A61L 31/14* (2006.01)
*A61L 27/26* (2006.01)
*A61L 31/04* (2006.01)
*A61L 31/12* (2006.01)
*A61L 27/44* (2006.01)

(52) U.S. Cl.
CPC ............ *A61L 31/041* (2013.01); *A61L 31/06* (2013.01); *A61L 31/128* (2013.01); *A61L 31/14* (2013.01); *A61L 2400/16* (2013.01); *A61M 2205/0266* (2013.01)

(56) References Cited

U.S. PATENT DOCUMENTS

| | | | |
|---|---|---|---|
| 4,767,627 | A | 8/1988 | Caldwell et al. |
| 4,996,058 | A | 2/1991 | Sinnreich |
| 5,002,772 | A | 3/1991 | Curatolo et al. |
| 5,007,790 | A | 4/1991 | Shell |
| 5,443,843 | A | 8/1995 | Curatolo et al. |
| 5,840,332 | A | 11/1998 | Lerner et al. |
| 6,488,962 | B1 | 12/2002 | Berner et al. |
| 8,038,659 | B2 | 10/2011 | Boyden et al. |
| 8,377,453 | B2 | 2/2013 | Han et al. |
| 10,413,507 | B2 | 9/2019 | Zhang et al. |
| 10,517,819 | B2 | 12/2019 | Bellinger et al. |
| 10,517,820 | B2 | 12/2019 | Bellinger et al. |
| 10,532,027 | B2 | 1/2020 | Bellinger et al. |
| 10,596,110 | B2 | 3/2020 | Bellinger et al. |
| 10,610,482 | B2 | 4/2020 | Bellinger et al. |
| 10,716,751 | B2 | 7/2020 | Bellinger et al. |
| 10,716,752 | B2 | 7/2020 | Bellinger et al. |
| 2003/0092964 | A1 | 5/2003 | Kim et al. |
| 2004/0180086 | A1 | 9/2004 | Ramtoola et al. |
| 2005/0175702 | A1 | 8/2005 | Muller-Schulte |
| 2006/0142794 | A1* | 6/2006 | Lendlein ............... A61F 6/00 606/191 |
| 2007/0112370 | A1* | 5/2007 | Andrews ........... A61M 25/1029 606/194 |
| 2007/0129784 | A1 | 6/2007 | Lendlein |
| 2007/0264307 | A1 | 11/2007 | Chen et al. |
| 2008/0153779 | A1 | 6/2008 | Liao et al. |
| 2008/0249156 | A1 | 10/2008 | Palepu |
| 2009/0092415 | A1 | 4/2009 | Murakami et al. |
| 2009/0246142 | A1 | 10/2009 | Bhatia et al. |
| 2010/0266655 | A1 | 10/2010 | Dadey |
| 2011/0052700 | A1 | 3/2011 | Han et al. |
| 2011/0174653 | A1* | 7/2011 | Schwarz ................ A61J 3/071 206/461 |
| 2012/0321706 | A1 | 12/2012 | Masri et al. |
| 2013/0226104 | A1 | 8/2013 | Hyde et al. |
| 2013/0273135 | A1 | 10/2013 | Brooks et al. |
| 2017/0051099 | A1 | 2/2017 | DiCiccio et al. |
| 2017/0106099 | A1 | 4/2017 | Bellinger et al. |
| 2017/0128576 | A1 | 5/2017 | Zhang et al. |
| 2017/0135954 | A1 | 5/2017 | Bellinger et al. |
| 2017/0266112 | A1 | 9/2017 | Bellinger et al. |
| 2019/0125667 | A1 | 5/2019 | Bellinger et al. |
| 2019/0133936 | A1 | 5/2019 | Bellinger et al. |
| 2019/0175500 | A1 | 6/2019 | Bellinger et al. |
| 2019/0231697 | A1 | 8/2019 | Bellinger et al. |
| 2019/0254966 | A1 | 8/2019 | Bellinger et al. |
| 2019/0262265 | A1 | 8/2019 | Bellinger et al. |
| 2019/0298652 | A1 | 10/2019 | Bellinger et al. |
| 2020/0030234 | A1 | 1/2020 | Zhang et al. |
| 2020/0085736 | A1 | 3/2020 | Bellinger et al. |
| 2020/0085737 | A1 | 3/2020 | Bellinger et al. |

FOREIGN PATENT DOCUMENTS

| | | | |
|---|---|---|---|
| EP | 2329810 A1 | | 6/2011 |
| JP | 2006-518392 A | | 8/2006 |
| JP | 2007-314797 A | | 12/2007 |
| JP | 2017-524662 A | | 8/2017 |
| WO | WO 03/015745 A1 | | 2/2003 |
| WO | WO 2004/073690 A1 | | 9/2004 |
| WO | WO 2007/013059 A2 | | 2/2007 |
| WO | WO 2007/048223 A2 | | 5/2007 |
| WO | WO 2014/014348 A1 | | 1/2014 |

OTHER PUBLICATIONS

Mohr et al., Initiation of shape-memory effect by inductive heating of magnetic nanoparticles in thermoplastic polymers. Proc Natl Acad Sci U S A. Mar. 7, 2006;103(10):3540-5. Epub Feb. 28, 2006.
Zhang et al., Biodegradable shape memory nanocomposites with thermal and magnetic field responsiveness. J Biomater Sci Polym Ed. 2013;24(9):1057-70. doi: 10.1080/09205063.2012.735098. Epub Oct. 15, 2012.
European Exam Report dated Mar. 19, 2019 for Application No. EP 16724767.5.
International Preliminary Report on Patentability dated Nov. 16, 2017 for Application No. PCT/US2016/030020.
[No Author Listed], Wound Closure Manual. Ethicon, Inc. A Johnson and Johnson company. 2005. 127 pages.
Ajili et al., Polyurethane/polycaprolactane blend with shape memory effect as a proposed material for cardiovascular implants. Acta Biomaterialia. 2009;5(5): 1519-30. doi:10.1016/j.actbio.2008.12.014.
Belknap et al., Feasibility of an ingestible sensor-based system for monitoring adherence to tuberculosis therapy. Plos One. Jan. 2013;8(1):e53373(1-5).
Byrne et al., The ingestible telemetric body core temperature sensor: a review of validity and exercise applications. Brit J Sport Med. 2007;41:126-33, doi:10.1136/bjsm.2006.026344.
Cargill et al., Controlled gastric emptying. 1. Effects of physical properties on gastric residence times of nondisintegrating geometric shapes in beagle dogs. Pharm Res. Aug. 1988;5(8):533-6.
Ereqat et al., MDR tuberculosis and non-compliance with therapy. Lancet Infect Dis. Sep. 2011;11(9):662. doi: 10.1016/S1473-3099(11)70227-4.
Fallon et al., The surgical management of Rapunzel syndrome: a case series and literature review. J Pediatr Surg. Apr. 2013;48(4):830-4. doi: 10.1016/j.jpedsurg.2012.07.046.
Fuhrmann et al. Sustained gastrointestinal activity of dendronized polymer-enzyme conjugates. Nat Chem. Jul. 2013; 5:582-9, doi: 10.1038/Nchem.1675.
Genco et al., Bioenterics intragastric balloon: The Italian experience with 2,515 patients. Obes Surg. 2005; 15:1161-4, doi: 10.1381/0960892055002202.
Gordi et al., Pharmacokinetics of gabapentin after a single day and at steady state following the administration of gastric-retentive-extended-release and immediate-release tablets: a randomized, open-label, multiple-dose, three-way crossover, exploratory study in healthy subjects. Clin Ther. May 2008;30(5):909-16. doi: 10.1016/j.clinthera.2008.05.008.
Huang et al., Shape memory materials. Materials Today. Jul.-Aug. 2010;13(7-8):54-61. doi:10.1016/S1369-7021(10)70128-0.
Hwang et al., Gastric retentive drug-delivery systems. Crit Rev Ther Drug Carrier Syst. 1998;15(3):243-84.
Kethu et al., Endoluminal bariatric techniques. Gastrointestinal endoscopy. 2012;76(1):1-7, doi:10.1016/j.gie.2012.02.020.
Khanna et al., Epoxy resin beads as a pharmaceutical dosage form I: method of preparation. J Pharm Sci. Jun. 1969;58(9):1114-7.
Kim et al., Polyurethanes having shape memory effects. Polymer. 1996;37(26):5781-93. doi:10.1016/S0032-3861(96)00442-9.

(56) References Cited

OTHER PUBLICATIONS

Kim et al., Biologically derived melanin electrodes in aqueous sodium-ion energy storage devices. P Natl Acad Sci USA. Dec. 24, 2013;110(252): 20912-17, doi: 10.1073/pnas.1314345110.

Lam et al., Advanced progress of microencapsulation technologies: In vivo and in vitro models for studying oral and transdermal drug deliveries. J. Control Release. 2014; 178,:25-45.

Laulicht et al., Localization of magnetic pills. Proc Natl Acad Sci. Feb. 8, 2011;108:2252-7, doi:10.1073/pnas.1016367108.

Liu et al., Review of electro-active shape-memory polymer composite. Compos Sci and Technol. 2009;69(13): 2064-8. doi:10.1016/j.compscitech.2008.08.016.

Meng et al., A review of shape memory polymer composites and blends. Composites Part A: Applied Science and Manufacturing. 2009;40(11):1661-72. doi:10.1016/j.compositesa.2009.08.011.

Moes, Gastroretentive dosage forms. Crit Rev Ther Drug Carrier Syst. 1993;10: 143-195. Submitted in 3 parts.

Munk et al., Gastrointestinal motility in health and disease (ed H. L. Duthie) Ch. 38, 349-359 (Springer Netherlands, 1978).

Salessiotis, Measurement of the diameter of the pylorus in man: Part I. Experimental project for clinical application. The Amer J of Surgery. Sep. 1972; 124:331-3, doi:http://dx.doi.org/10.1016/0002-9610(72)90036-0.

Singh et al., Floating drug delivery systems: an approach to oral controlled drug delivery via gastric retention. J Control Release. Feb. 3, 2000;63(3):235-59.

Tao et al. Silk-based conformal, adhesive, edible food sensors. Adv Mater. 2012; 24:1067-72, doi:10.1002/adma.201103814.

Traverso et al., Special delivery for the gut. Nature. Mar. 26, 2015;519:S19.

Won et al. Oligopeptide complex for targeted non-viral gene delivery to adipocytes. Nat Mater. Dec. 2014;13:1157-64, doi: 10.1038/Nmat4092.

Neto-Ferreira et al., Pleiotropic effects of rosuvastatin on the glucose metabolism and the subcutaneous and visceral adipose tissue behavior in C57Bl/6 mice. Diabetology Metabol Synd. 2013;5:32, 10 pages.

* cited by examiner

TRIGGERABLE SHAPE MEMORY INDUCTION DEVICES

RELATED APPLICATIONS

This application claims priority under 35 U.S.C. § 119(e) to U.S. Provisional Application Ser. No. 62/156,000, filed May 1, 2015, which is incorporated herein by reference in its entirety for all purposes.

FIELD OF THE INVENTION

This invention generally relates to triggerable shape memory compositions and devices, and related methods.

BACKGROUND OF THE INVENTION

Drug efficacy is dependent on adherence of a patient to medication. In spite of health risks associated with poor medical adherence, nearly half of patients do not adhere to their prescribed regimen. Delivery devices enabling extended release provide a potential solution to this problem by allowing the administration of a single dose, which would release drugs over a prolonged period of time. However, a key challenge that remains is the on-demand exit from the body and safe passage through the lower gastrointestinal tract when drug administration is no longer required. Accordingly, new materials and methods are needed.

SUMMARY OF THE INVENTION

The present invention generally relates to triggerable shape memory compositions and devices, and related methods.

In one aspect, methods are provided. In some embodiments, the method comprises stimulating a device such that the device obtains a second configuration, wherein the second configuration is sufficiently small such that the device is removed from the location internally of the subject, wherein the device has a first configuration different than the second configuration prior to stimulating, wherein the second configuration has a largest cross-sectional dimension at least about 10% less than a largest cross-sectional dimension of the first configuration, and/or wherein the second configuration has a convex hull at least about 10% less than a convex hull of the first configuration.

In some embodiments, the method comprises administering a device having a first configuration, wherein the device obtains a second configuration in the location internally of the subject such that the device is retained within the location, stimulating, after a period of time, the device such that the device obtains the first configuration, wherein the first configuration is such that device is removed from the location.

In another aspect, compositions are provided. In some embodiments, the composition comprises a polymer network comprising a first polymeric material and a second polymeric material, a plurality of non-polymeric portions associated with the polymer network which, upon exposure to an external stimulus, facilitate heating of the first polymeric material to at least about 45° C., wherein the first polymeric material has a softening temperature of greater than or equal to about 45° C., wherein the polymer network is constructed and arranged to have a first configuration below the softening temperature of the first polymeric material and a second configuration different than the first configuration above the softening temperature of the first polymeric material, and wherein the second configuration has a largest cross-sectional dimension at least about 10% less than a largest cross-sectional dimension of the first configuration, and/or wherein the second configuration has a convex hull at least about 10% less than a convex hull of the first configuration.

In some embodiments, the composition comprises a polymer network comprising a first polymeric material and a second polymeric material, a plurality of paramagnetic particles associated with the polymer network, wherein the first polymeric material is a non-crosslinked polymer having a softening temperature of greater than or equal to about 45° C., wherein the second polymeric material is a crosslinked polymer, wherein the polymer network is constructed and arranged to have a first configuration below the softening temperature of the first polymeric material and a second configuration different than the first configuration above the softening temperature of the first polymeric material, wherein the second configuration has a largest cross-sectional dimension at least about 10% less than a largest cross-sectional dimension of the first configuration, and/or wherein the second configuration has a convex hull at least about 10% less than a convex hull of the first configuration.

In yet another aspect, devices are provided. In some embodiments, the device comprises an expanded profile in which the device, when positioned at a location internally of the subject, is retained at that location under normal physiological conditions, the device being susceptible to a stimulus applied from externally of the subject whereby the device assumes a contracted profile and is eliminated from the location internally of the subject.

Other advantages and novel features of the present invention will become apparent from the following detailed description of various non-limiting embodiments of the invention when considered in conjunction with the accompanying figures. In cases where the present specification and a document Incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION OF THE INVENTION

Figure 1A:
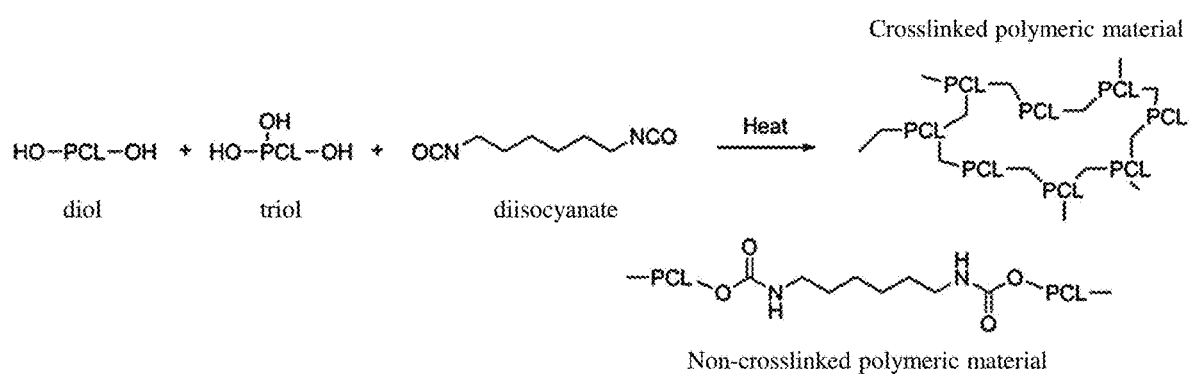
FIG. 1A is a schematic of shape memory properties, according to one set of embodiments.

In accordance with the invention, compositions, devices, and related methods have been developed for medical-related and other applications. In some embodiments, the devices and compositions described herein comprise a triggerable shape memory polymer network. In certain embodiments, the polymer network comprises a covalently cross-linked polymeric material and a non-crosslinked polymeric material associated with the crosslinked polymeric material. In some cases, the polymer network has a first configuration (e.g., as polymerized), and a second configuration (e.g., upon heating and deformation), such that the polymer network can be triggered to recover the first configuration upon heating the polymeric material above a softening temperature of the polymeric material. In certain embodiments, the polymer network comprises a plurality of particles capable of increasing the temperature of the polymer network (e.g., above the softening temperature) in the presence of an external stimulus such as induction, radio frequency, or magnetic resonance, such that the polymer network changes configuration. The polymeric material may be molded into any suitable shape.

The compositions and devices described herein may be useful, for example, in biomedical applications such as in retention devices. In some embodiments, methods for deploying and/or removing a retention device, such as a gastric retention device, are provided. The retention device may be removed internally from a subject by, for example, remotely stimulating the polymer network such that the polymer network changes configuration. The term "subject," as used herein, refers to an individual organism, for example, a human or an animal. In some embodiments, the subject is a mammal (e.g., a human, a non-human primate, or a non-human mammal), a vertebrate, a laboratory animal, a domesticated animal, an agricultural animal, or a companion animal. In some embodiments, the subject is a human. In some embodiments, the subject is a rodent, a mouse, a rat, a hamster, a rabbit, a dog, a cat, a cow, a goat, a sheep, or a pig.

The compositions, devices, and methods described herein offer several advantages over traditional materials (e.g., shape memory materials) and traditional retention devices, including the ability to remotely trigger a change in the configuration of the device and/or induce the exit of the device internal to a subject. The compositions and devices described herein are generally biocompatible and undergo local induction heating at temperatures well below the temperature at which the tissue of a subject would be injured (e.g., burned). The compositions and devices described herein may be loaded with bioactive compounds such as drugs and/or folded into a capsule for oral delivery.

In some embodiments, the triggerable shape memory composition comprises a polymer network. In certain embodiments, the polymer network comprises two or more polymeric materials. In some cases, at least one of the two or more polymeric materials comprises a non-crosslinked polymeric material and at least one of the two or more polymeric materials comprises a covalently crosslinked polymeric material. Non-crosslinked polymeric materials, as described herein, generally comprise a polymeric backbone, optionally substituted, optionally branched, but does not comprise a covalent crosslink with other polymeric materials. In some embodiments, the non-crosslinked polymeric material comprises one or more crystalline domains below a softening temperature of the non-crosslinked polymeric material.

In some embodiments, the polymer network may be formed by the reaction of a first bifunctional polymeric material, a trifunctional polymeric material, and a second bifunctional polymeric material or bifunctional oligomeric material different than the first bifunctional polymeric material. Non-limiting examples of suitable functional groups include amines, carboxylic acids, alcohols and thiols.

In some embodiments, the polymer network comprises a polymeric repeat structure as in Formula (I):

wherein each R is the same or different and is H, O, an alkyl group, provided at least one R is oxygen, wherein m is 1-10, and wherein n is 1-5000.

In some embodiments, m is 1-3, 2-4, 3-6, 4-8, or 5-10. In an exemplary embodiment, m is 6.

In certain embodiments, n is 1-100, 1-1000, 50-500, 250-750, 500-1000, 500-2000, 1000-4000, or 2500-5000.

In an exemplary embodiment, the polymer network comprises a polymeric repeat structure as in Formula (II):

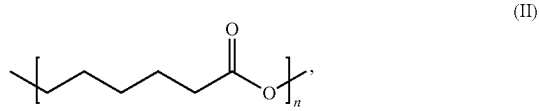

(II)

wherein n is 1-1000. In some such embodiments, the polymer network comprises polycaprolactone (PCL).

In another exemplary embodiment, the polymer network comprises a polymeric repeat structure as in Formula (III):

(III)

wherein n is 1-1000. In some such embodiments, the polymer network comprises polylactic acid (PLA).

In certain embodiments, the polymer network comprises a first polymeric material (e.g., a non-crosslinked polymeric material) and a second polymeric material (e.g., a covalently crosslinked polymeric material).

In certain embodiments, the first polymeric material is formed by the reaction of a diol polymer comprising the structure as in Formula (I) and a diisocyanate. In some embodiments, the diisocyanate has a structure as in Formula (IV):

(IV)

wherein x is 1-10. In some embodiments, x is 1-3, 2-4, 3-6, 4-8, or 5-10. For example, in some embodiments, the first polymeric material is formed by the reaction of a diol-polycaprolactone and/or a diol-polylactic acid with a diisocyanate.

In some embodiments, the second polymeric material is formed by the reaction of the diol polymer comprising the structure as in Formula (I), a triol polymer comprising the structure as in Formula (I), and a diisocyanate (e.g., as in Formula (IV)). For example, in some embodiments, the second polymeric material is formed by the reaction of a triol-polycaprolactone and/or a triol-polylactic acid with a diisocyanate. FIG. 1A shows a non-limiting example scheme of a reaction of a diol polymer, a triol polymer, and a diisocyanate, as described herein, such that a first polymeric material (e.g., a non-crosslinked polymeric material) and a second polymeric material (e.g., a covalently crosslinked polymeric material) is formed. While the description herein focuses primarily on triol polymers comprising the structure as in Formula (I), those skilled in the art would be capable of selecting higher order functionality polymers (e.g., tetra-, penta-, hexa-) for reacting with the diol polymer and diisocyanate, based upon the teachings of this specification.

In certain embodiments, the polymer network comprising the first polymeric material and the second polymeric material is formed by the reaction of a mixture of a diol comprising the structure as in Formula (I), a triol comprising the structure as in Formula (I), and a diisocyanate. The diol polymer and triol polymer may be present in the mixture at any suitable ratio including, for example, between about 1:5 and about 5:1. In some embodiments, the ratio of diol polymers to triol polymers present in the mixture is at least about 1:5, at least about 1:4, at least about 1:3, at least about 1:2, or at least about 1:1, at least about 2:1, at least about 3:1, or at least about 4:1. In certain embodiments, the ratio of diol polymers to triol polymers present in the mixture is less than or equal to about 5:1, less than or equal to about 4:1, less than or equal to about 3:1, less than or equal to about 2:1, less than or equal to about 1:1, less than or equal to about 1:2, less than or equal to about 1:3, or less than or equal to about 1:4. Combinations of the above referenced ranges are also possible (e.g., between 1:5 and 5:1, between 1:1 and 4:1, between 2:1 and 4:1). In an exemplary embodiments, the ratio of diol polymers to triol polymers is about 3:1.

In some cases, the diisocyanate may be present in the mixture in any suitable amount. For example, in some embodiments, the diisocyanate is present in the mixture such that the ratio of isocyanate groups (—NCO) to hydroxyl groups (—OH) is between about 1:1 and about 1.1:1. In some embodiments, the ratio of isocyanate groups to hydroxyl groups present in the mixture is at least about 1:1 or at least about 1.05:1. In certain embodiments, the ratio of isocyanate groups to hydroxyl groups present in the mixture is less than or equal to about 1.1:1, or less than or equal to about 1.05:1. Combinations of the above-referenced ranges are also possible (e.g., between 1:1 and 1.1:1).

The mixture of a diol comprising the structure as in Formula (I), a triol comprising the structure as in Formula (I), and a diisocyanate may be reacted at any suitable temperature. For example, in some embodiments, the mixture is reacted at a reaction temperature ranging between about 50° C. and about 90° C. In some embodiments, the reaction temperature is at least about 50° C., at least about 60° C., at least about 70° C., or at least about 80° C. In certain embodiments, the reaction temperature is less than or equal to about 90° C., less than or equal to about 80° C., less than or equal to about 70° C., or less than or equal to about 60° C. Combinations of the above referenced ranges are also possible (e.g., between 50° C. and 90° C., between 60° C. and 80° C.).

In some embodiments, the mixture may be poured into a mold and cured at any suitable reaction temperature, as described above. In some cases, the mixture may be cured in the mold for at least about 4 hours, at least about 12 hours, or at least about 24 hours.

While the description above is related primarily to diol and diisocyanate reactions, those skilled in the art would be capable of selecting other suitable polymeric materials comprising other functional groups based upon the teachings of this specification. In some embodiments, the non-cross-linked polymeric material is associated with the covalently crosslinked polymeric material. Without wishing to be bound by theory, the two polymeric materials may be associated via hydrogen bonds and/or entanglement.

The polymeric materials described herein may have a particular softening temperature. In some embodiments, the softening temperature is the glass transitional temperature of the polymeric material. In certain embodiments, the softening temperature is the melting temperature of the polymeric material. In some cases, the first polymeric material has a first softening temperature and the second polymeric material has a second softening temperature different than the first softening temperature. In some cases, the first softening temperature is greater than the second softening temperature. In certain embodiments, the first softening temperature is less than the second softening temperature.

In some embodiments, the softening temperature of the polymeric material (e.g., the first polymeric material, the second polymeric material) is between about 37° C. and about 65° C. In certain embodiments, the softening temperature of the polymeric material is at least about 37° C., at least about 45° C., at least about 50° C., at least about 55° C., or at least about 60° C. In some embodiments, the softening temperature is less than or equal to about 65° C., less than or equal to about 60° C., less than or equal to about 55° C., less than or equal to about 50° C., or less than or equal to about 45° C. Combinations of the above referenced ranges are also possible (e.g., between 45° C. and 65° C.).

In an exemplary embodiment, the first polymeric material has a melting temperature between 45° C. and 65° C. and the second polymeric material has a melting temperature greater than 65° C.

In some embodiments, the polymer network is heated to a temperature above the softening temperature of the first polymeric material such that the polymer network changes configuration. The polymer network may have any suitable configuration. In some embodiments, the polymer network has a particular shape as defined by a cross-sectional area of the polymer network. Non-limiting examples of suitable cross-sectional shapes include square, circles, ovals, polygons, tubes, rings, star, or the like. Those skilled in the art would be capable of selecting suitable shapes depending on the application and based upon the teachings of this specification.

In some embodiments, the polymer network comprises the first polymeric material and the second polymeric material has a first configuration below the softening temperature of the first polymeric material and/or the second polymeric material, and a second configuration different than the first configuration above the softening temperature.

In certain embodiments, the configuration of the polymer network may be characterized by a largest cross-sectional dimension. In some embodiments, the largest cross-sectional dimension of the first configuration may be at least about 10% less, at least about 20% less, at least about 40% less, at least about 60% less, or at least about 80% less than the largest cross-sectional dimension of the second configuration. In certain embodiments, the largest cross-sectional dimension of the second configuration may be at least about 10% less, at least about 20% less, at least about 40% less, at least about 60% less, or at least about 80% less than the largest cross-sectional dimension of the first configuration.

Figure 1B:
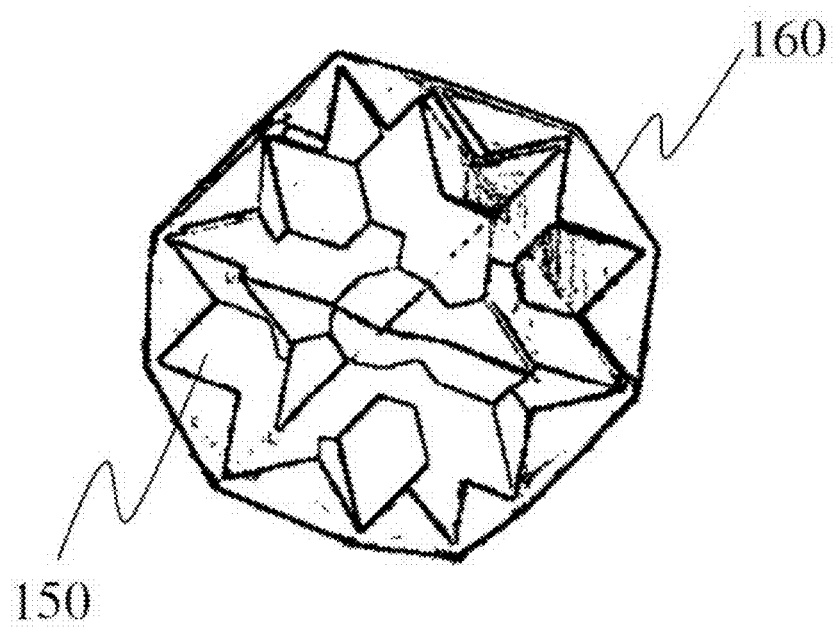
FIG. 1B is a schematic of the convex hull of a polymer network, according to one set of embodiments.

In some embodiments, the configuration of the polymer network may be characterized by a convex hull volume of the polymer network. The term convex hull volume is known in the art and generally refers to a set of surfaces defined by the periphery of a 3-D object such that the surfaces define a particular volume. For example, as illustrated in FIG. 1B, a 3D star-like object 150 has a convex hull volume as defined by convex hull 160. In some embodiments, the convex hull volume of the first configuration may be at least about 10% less, at least about 20% less, at least about 40% less, at least about 60% less, or at least about 80% less than the convex hull volume of the second configuration. In certain embodiments, the convex hull volume of the second configuration may be at least about 10% less, at least about 20% less, at least about 40% less, at least about 60% less, or at least about 80% less than the convex hull volume of the first configuration. Other ranges are also possible.

Those skilled in the art would understand that the differences between the first configuration and the second configuration do not refer to a swelling or a shrinking of the structure (e.g., in the presence of a solvent), but instead refers to a change in shape and/or orientation of at least a portion of the structure (e.g., in the presence of a stimulus such as heat and/or mechanical pressure/compression), although some degree of swelling or shrinking may occur between the two configurations.

In some embodiments, the first configuration is constructed and arranged such that a device comprising the polymer network is retained at a location internal of a subject, and the second configuration is constructed and arranged such that the device may exit the location internally in a subject. In some cases, the first configuration is sufficiently large such that the device is retained at a location internal of the subject and the second configuration is sufficiently small such that the device may exit the location internally in a subject.

In an exemplary embodiment, a device comprising the polymer network is located internally to a subject at a first location and has a first configuration and, upon stimulation, the device obtains a second configuration such that the device moves to a second location internal to a subject different than the first location.

Figure 2:
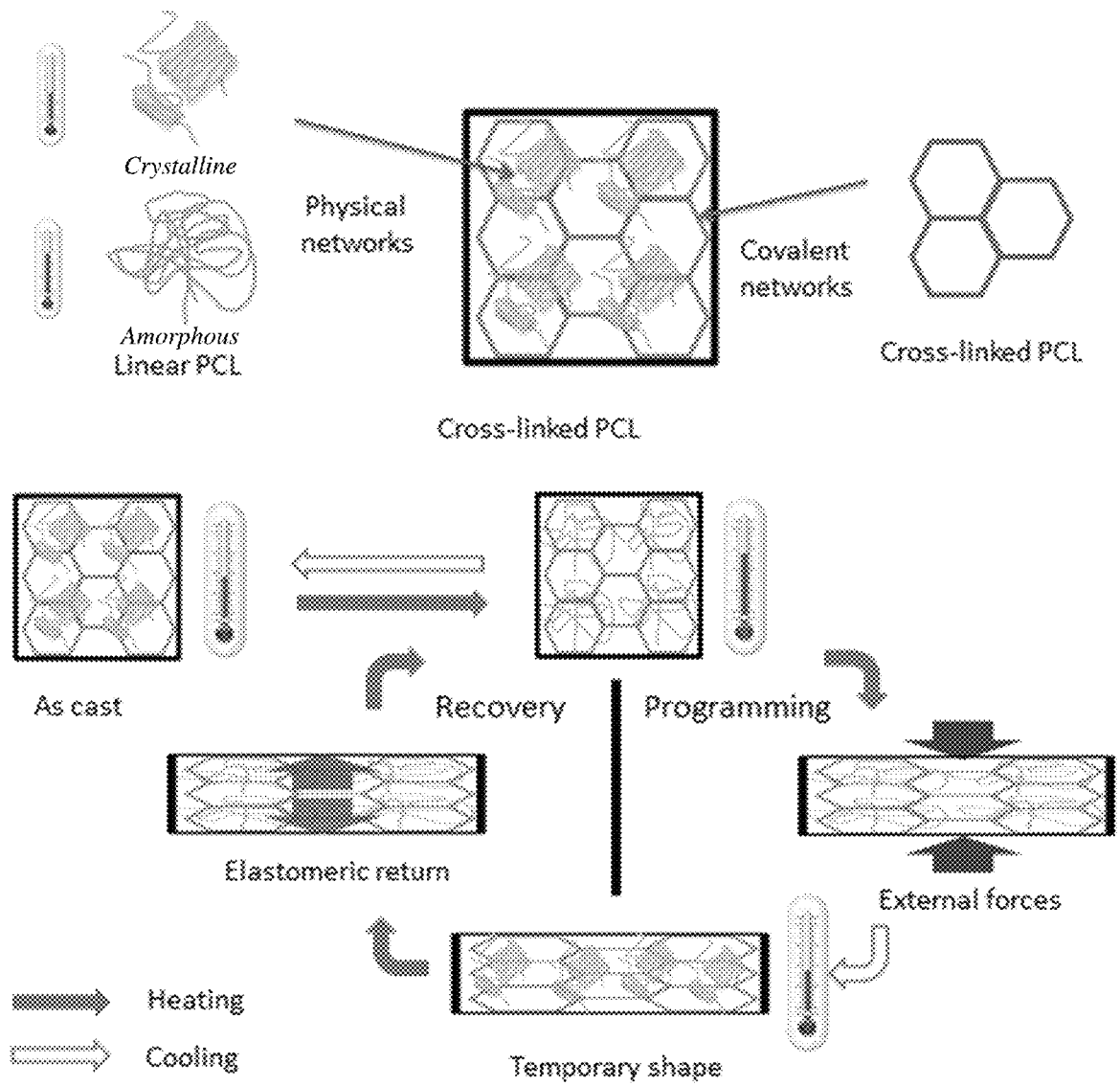
FIG. 2 is an exemplary reaction scheme for a polymer network, according to one set of embodiments.

In certain embodiments, the polymer network may be polymerized and cast in a first configuration, mechanically deformed in the presence of heat (e.g., above the softening temperature of the first polymeric material) such that the polymer network obtains a second configuration, and cooled (e.g., to room temperature). For example, the polymer network comprising a non-crosslinked polymeric material and a crosslinked polymer material may be cast in a first configuration at a first temperature below the softening temperature of the non-crosslinked polymeric material. The polymer network may then be heated to a temperature above the softening temperature of the non-crosslinked polymeric material (e.g., such that crystalline domains become amorphous) and mechanically deformed to a obtain a second configuration. The polymer network may be mechanically deformed using any suitable method including, for example, bending, twisting, folding, molding (e.g., pressing the material into a mold having a new shape), expanding (e.g., applying a tensile force to the material), compressing, and/or wrinkling the polymer network. The polymer network may be cooled after mechanically deforming the polymer network such that the second configuration is maintained. As described herein, the polymer network may be stimulated (e.g., heated to a temperature above the softening temperature of the first polymeric material) such that the polymer network obtains the first configuration. Such shape memory processes described above are illustrated schematically in FIG. 2.

The polymer network may maintain the second configuration for any suitable duration prior to stimulation. Advantageously, the polymer networks described herein may have relatively long shelf lives in the first or second configurations. In some embodiments, the second configuration may be stable under ambient conditions (e.g., room temperature, atmospheric pressure and relative humidity) and/or physiological conditions (e.g., at or about 37° C., in physiologic fluids) for at least about 1 day, at least about 3 days, at least about 7 days, at least about 2 weeks, at least about 1 month, at least about 2 months, or for at least about 6 months.

In some embodiments, the polymer network in the second configuration may be triggered (i.e. stimulated) such that the polymer network reverts to the first configuration. Stimulating In some embodiments, stimulating the polymer network comprises heating the polymer network (e.g., to a temperature above the softening temperature of the first polymeric material). The polymer network may be heated using any suitable method including, for example, applying hot air, placing the polymer network on a substrate and heating the substrate, submerging at least a portion of the polymer network in a heated liquid, or the like. In embodiments in which the polymer network in located internal to a subject, the subject may drink a heated liquid to heat the polymer network. In some embodiments, the polymer network may be stimulated via an external stimulus, such that the polymer network is heated to a temperature above the softening temperature of the first polymeric material.

In some embodiments, the polymer network described herein comprises a plurality of non-polymeric portions. In some embodiments, the non-polymeric portions comprise non-polymeric particles. The plurality of non-polymeric materials, in some cases, may be exposed to a stimulus, such that the plurality of non-polymeric materials facilitate heating of the polymer network to a temperature greater than the softening temperature of the first and/or second polymeric materials. Advantageously, the exposure of the non-polymeric material to an external stimulus does not heat the non-polymeric material, and does not heat the polymer network, to a temperature greater than 65° C. (e.g., to prevent burns of a subject in which the polymer network is internally located). In some embodiments, the plurality of non-polymeric materials may be stimulated such that the first polymeric material is heated to a temperature above its softening temperature (e.g., at least about 45° C.). In some embodiments, the plurality of non-polymeric materials may be stimulated such that the temperature of the polymer network is less than the softening temperature of the second polymeric material.

The plurality of non-polymeric particles may comprise any suitable material. Non-limiting examples of suitable materials include, for example, paramagnetic particles such as low carbon iron particles, pure iron, $Fe_3O_4$, $Fe_2O_3$. Those skilled in the art would be capable of selecting additional suitable non-polymeric particles for heating the polymer network upon exposure to a stimulus, based upon the teachings of this specification.

In some embodiments, the non-polymeric particles have a particular size. In some embodiments, the non-polymeric particles have an average diameter of between 1 micron and 2 mm. In certain embodiments, the non-polymeric particles have an average diameter of at least about 1 micron, at least about 5 microns, at least about 10 microns, at least about 50 microns, at least about 100 microns, at least about 500 microns, at least about 750 microns, at least about 1 mm, or at least about 1.5 mm. In some embodiments, the non-polymeric particles have an average diameter of less than or equal to about 2 mm, less than or equal to about 1.5 mm, less than or equal to about 1 mm, less than or equal to about 750 microns, less than or equal to about 500 microns, less than or equal to about 100 microns, less than or equal to about 50 microns, less than or equal to about 10 microns, or less than or equal to about 5 microns. Combinations of the above-referenced ranges are also possible (e.g., between 1 micron and 2 mm, between 5 microns and 100 microns, between 50 microns and 1000 microns, between 500 microns and 1.5 mm). Other ranges are also possible.

In certain embodiments, the non-polymeric particles have a particular ratio of surface area to volume. In some embodiments, the ratio of surface area to volume of the non-polymeric particles ranges between 1 $mm^{-1}$ and 1000 $mm^{-1}$ (e.g., between 1 $mm^{-1}$ and 3 $mm^{-1}$, between 1 $mm^{-1}$ and 5 $mm^{-1}$, between 3 $mm^{-1}$ and 8 $mm^{-1}$, between 8 $mm^{-1}$ and 600 $mm^{-1}$, between 8 $mm^{-1}$ and 1000 $mm^{-1}$).

In some embodiments, the stimulus described herein is an external stimulus. Non-limiting examples of external stimuli include application of radio waves (e.g., via radio-frequency induction), application of magnetic resonance (e.g., via exposure to an MRI), or other induction methods. For example, in certain embodiments, an external stimulus such as radio frequency induction is applied proximate a subject such that the polymer network comprising a plurality of non-polymeric particles, as described herein, located internally to a subject increases in temperature (e.g., via heating of the non-polymeric particles).

The polymer networks described herein may be useful in a number of applications including, for example, retention devices. In some embodiments, a device (e.g., a retention device) comprising the polymer network has an expanded profile in which the device, when positioned at a location internally of the subject, is retained at that location under normal physiological conditions. In some such embodiments, as described above, the device is susceptible to a stimulus applied from externally of the subject whereby the device assumes a contracted profile and is eliminated from the location internally of the subject.

The device may be retained internally of the subject in locations such as the stomach, the bladder, the esophagus, the colon, or the like. In a particular embodiments, the device is a gastric retention device.

In some embodiments, the polymer network is cast in a first configuration and heated and mechanically deformed such that it obtains a second configuration. The second configuration may be compressed and/or deformed into a capsule for, for example, oral administration of the polymer network. In some embodiments, the polymer network (or capsule containing the polymer network) may be administered orally, administered endoscopically, or administered cytoscopically. In some such embodiments, the capsule may dissolve and/or open such that the polymer network is located internally of a subject in a desired location. Upon dissolving and/or opening of the capsule, the polymer network may recover the second configuration. In certain embodiments, as described herein, the polymer network may then be externally triggered (i.e. stimulated) such that the polymer network obtains the first configuration. In some such embodiments, the first configuration permits elimination of the device from the desired location. In certain embodiments, elimination occurs under normal physiological conditions. In some cases, elimination may be stimulated by the drinking of a hot beverage (e.g., such that the polymer network reaches a temperature above the softening temperature of the first polymeric material).

Devices described herein may be useful for monitoring, obesity treatment, and/or drug delivery applications. For example, the devices described herein may be useful in the treatment of type 2 diabetes, gastroesophageal reflux diseases and other chronic diseases. In certain embodiments, devices comprising polymer networks described herein can be used as a platform for loading edible electronic devices.

Any terms as used herein related to shape, orientation, alignment, and/or geometric relationship of or between, for example, one or more articles, compositions, structures, materials and/or subcomponents thereof and/or combinations thereof and/or any other tangible or intangible elements not listed above amenable to characterization by such terms, unless otherwise defined or indicated, shall be understood to not require absolute conformance to a mathematical definition of such term, but, rather, shall be understood to indicate conformance to the mathematical definition of such term to the extent possible for the subject matter so characterized as would be understood by one skilled in the art most closely related to such subject matter. Examples of such terms related to shape, orientation, and/or geometric relationship include, but are not limited to terms descriptive of: shape—such as, round, square, circular/circle, rectangular/rectangle, triangular/triangle, cylindrical/cylinder, eliptical/ellipse, (n)polygonal/(n)polygon, etc.; angular orientation—such as perpendicular, orthogonal, parallel, vertical, horizontal, collinear, etc.; contour and/or trajectory—such as, plane/planar, coplanar, hemispherical, semi-hemispherical, line/linear, hyperbolic, parabolic, flat, curved, straight, arcuate, sinusoidal, tangent/tangential, etc.; surface and/or bulk material properties and/or spatial/temporal resolution and/or distribution—such as, smooth, reflective, transparent, clear, opaque, rigid, impermeable, uniform(ly), inert, non-wettable, insoluble, steady, invariant, constant, homogeneous, etc.; as well as many others that would be apparent to those skilled in the relevant arts. As one example, a fabricated article that would described herein as being "square" would not require such article to have faces or sides that are perfectly planar or linear and that intersect at angles of exactly 90 degrees (indeed, such an article can only exist as a mathematical abstraction), but rather, the shape of such article should be interpreted as approximating a "square," as defined mathematically, to an extent typically achievable and achieved for the recited fabrication technique as would be understood by those skilled in the art or as specifically described.

As used herein, the term "react" or "reacting" refers to the formation of a bond between two or more components to produce a stable, isolable compound. For example, a first component and a second component may react to form one reaction product comprising the first component and the second component joined by a covalent bond. The term "reacting" may also include the use of solvents, catalysts, bases, ligands, or other materials which may serve to promote the occurrence of the reaction between component(s). A "stable, isolable compound" refers to isolated reaction products and does not refer to unstable intermediates or transition states.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. The alkyl groups may be optionally substituted, as described more fully below. Examples of alkyl groups include, but are not limited to, methyl, ethyl, propyl, iso-propyl, butyl, isobutyl, tert-butyl, 2-ethylhexyl, cyclopropyl, cyclobutyl, cyclopentyl, cyclohexyl, and the like. "Heteroalkyl" groups are alkyl groups wherein at least one atom is a heteroatom (e.g., oxygen, sulfur, nitrogen, phosphorus, etc.), with the remainder of the atoms being carbon atoms. Examples of heteroalkyl groups include, but are not limited to, alkoxy, poly(ethylene glycol)-, alkyl-substituted amino, tetrahydrofuranyl, piperidinyl, morpholinyl, etc.

The terms "alkenyl" and "alkynyl" refer to unsaturated aliphatic groups analogous to the alkyl groups described above, but containing at least one double or triple bond respectively. The "heteroalkenyl" and "heteroalkynyl" refer to alkenyl and alkynyl groups as described herein in which one or more atoms is a heteroatom (e.g., oxygen, nitrogen, sulfur, and the like).

The term "aryl" refers to an aromatic carbocyclic group having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl), all optionally substituted. "Heteroaryl" groups are aryl groups wherein at least one ring atom in the aromatic ring is a heteroatom, with the remainder of the ring atoms being carbon atoms. Examples of heteroaryl groups include furanyl, thienyl, pyridyl, pyrrolyl, N lower alkyl pyrrolyl, pyridyl N oxide, pyrimidyl, pyrazinyl, imidazolyl, indolyl and the like, all optionally substituted.

The terms "amine" and "amino" refer to both unsubstituted and substituted amines, e.g., a moiety that can be represented by the general formula: N(R')(R'')(R''') wherein R', R'', and R''' each independently represent a group permitted by the rules of valence.

The terms "acyl," "carboxyl group," or "carbonyl group" are recognized in the art and can include such moieties as can be represented by the general formula:

wherein W is H, OH, O-alkyl, O-alkenyl, or a salt thereof. Where W is O-alkyl, the formula represents an "ester." Where W is OH, the formula represents a "carboxylic acid." In general, where the oxygen atom of the above formula is replaced by sulfur, the formula represents a "thiolcarbonyl" group. Where W is a S-alkyl, the formula represents a "thiolester." Where W is SH, the formula represents a "thiolcarboxylic acid." On the other hand, where W is alkyl, the above formula represents a "ketone" group. Where W is hydrogen, the above formula represents an "aldehyde" group.

As used herein, the term "heterocycle" or "heterocyclyl" refers to a monocyclic or polycyclic heterocyclic ring that is either a saturated ring or an unsaturated non-aromatic ring. Typically, the heterocycle may include 3-membered to 14-membered rings. In some cases, 3-membered heterocycle can contain up to 3 heteroatoms, and a 4- to 14-membered heterocycle can contain from 1 to about 8 heteroatoms. Each heteroatom can be independently selected from nitrogen, which can be quaternized; oxygen; and sulfur, including sulfoxide and sulfone. The terms "heterocycle" or "heterocyclyl" may include heteroaromatic or heteroaryl groups, as described more fully below. The heterocycle may be attached via any heteroatom ring atom or carbon ring atom. Representative heterocycles include morpholinyl, thiomorpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyrindinyl, tetrahydropyrimidinyl, tetrahydrothiophenyl, tetrahydrothiopyranyl, and the like. A heteroatom may be substituted with a protecting group known to those of ordinary skill in the art, for example, the hydrogen on a nitrogen may be substituted with a tert-butoxycarbonyl group. Furthermore, the heterocyclyl may be optionally substituted with one or more substituents (including without limitation a halogen atom, an alkyl radical, or aryl radical).

As used herein, the term "heteroaromatic" or "heteroaryl" means a monocyclic or polycyclic heteroaromatic ring (or radical thereof) comprising carbon atom ring members and one or more heteroatom ring members (such as, for example, oxygen, sulfur or nitrogen). Typically, the heteroaromatic ring has from 5 to about 14 ring members in which at least 1 ring member is a heteroatom selected from oxygen, sulfur, and nitrogen. In another embodiment, the heteroaromatic ring is a 5 or 6 membered ring and may contain from 1 to about 4 heteroatoms. In another embodiment, the heteroaromatic ring system has a 7 to 14 ring members and may contain from 1 to about 7 heteroatoms. Representative heteroaryls include pyridyl, furyl, thienyl, pyrrolyl, oxazolyl, imidazolyl, indolizinyl, thiazolyl, isoxazolyl, pyrazolyl, isothiazolyl, pyridazinyl, pyrimidinyl, pyrazinyl, triazinyl, triazolyl, pyridinyl, thiadiazolyl, pyrazinyl, quinolyl, isoquinolyl, indazolyl, benzoxazolyl, benzofuryl, benzothiazolyl, indolizinyl, imidazopyridinyl, isothiazolyl, tetrazolyl, benzimidazolyl, benzoxazolyl, benzothiazolyl, benzothiadiazolyl, benzoxadiazolyl, carbazolyl, indolyl, tetrahydroindolyl, azaindolyl, imidazopyridyl, qunizaolinyl, purinyl, pyrrolo[2,3]pyrimidyl, pyrazolo[3,4]pyrimidyl, benzo(b)thienyl, and the like. These heteroaryl groups may be optionally substituted with one or more substituents.

The term "substituted" is contemplated to include all permissible substituents of organic compounds, "permissible" being in the context of the chemical rules of valence known to those of ordinary skill in the art. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl" must still comprise the phenyl moiety and cannot be modified by substitution, in this definition, to become, e.g., a heteroaryl group such as pyridine. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

Examples of substituents include, but are not limited to, alkyl, aryl, aralkyl, cyclic alkyl, heterocycloalkyl, hydroxy, alkoxy, aryloxy, perhaloalkoxy, aralkoxy, heteroaryl, heteroaryloxy, heteroarylalkyl, heteroaralkoxy, azido, amino, halogen, alkylthio, oxo, acyl, acylalkyl, carboxy esters, carboxyl, carboxamido, nitro, acyloxy, aminoalkyl, alkylaminoaryl, alkylaryl, alkylaminoalkyl, alkoxyaryl, arylamino, aralkylamino, alkylsulfonyl, carboxamidoalkylaryl, carboxamidoaryl, hydroxyalkyl, haloalkyl, alkylaminoalkylcarboxy, aminocarboxamidoalkyl, alkoxyalkyl, perhaloalkyl, arylalkyloxyalkyl, and the like.

As used herein, the term "network" refers to a three dimensional substance having oligomeric or polymeric strands interconnected to one another by crosslinks.

As used herein, the term "strand" refers to an oligomeric or polymeric chain of one monomer unit, or an oligomeric or polymeric chain of two or more different monomer units.

As used herein, the term "backbone" refers to the atoms and bonds through which the monomer units are bound together. As used herein, the term "pendent group," when used in the context of the strand, refers to functional groups which are attached to the strand but do not participate in the bonds through which the monomer units are joined.

As used herein, the term "crosslink" refers to a connection between two strands. The crosslink may either be a chemical bond, a single atom, or multiple atoms. The crosslink may be formed by reaction of a pendant group in one strand with the backbone of a different strand, or by reaction of one pendant group with another pendant group. Crosslinks may exist between separate strand molecules, and may also exist between different points of the same strand.

As used herein, the terms "oligomer" and "polymers" each refer to a compound of a repeating monomeric subunit. Generally speaking, an "oligomer" contains fewer monomeric units than a "polymer." Those of skill in the art will appreciate that whether a particular compound is designated an oligomer or polymer is dependent on both the identity of the compound and the context in which it is used.

One of ordinary skill will appreciate that many oligomeric and polymeric compounds are composed of a plurality of compounds having differing numbers of monomers. Such mixtures are often designated by the average molecular weight of the oligomeric or polymeric compounds in the mixture. As used herein, the use of the singular "compound" in reference to an oligomeric or polymeric compound includes such mixtures.

The term "aliphatic group" refers to a straight-chain, branched-chain, or cyclic aliphatic hydrocarbon group and includes saturated and unsaturated aliphatic groups, such as an alkyl group, an alkenyl group, and an alkynyl group.

The term "alkoxy" refers to an alkyl group, as defined above, having an oxygen atom attached thereto. Representative alkoxy groups include methoxy, ethoxy, propyloxy, and tert-butoxy. An "ether" is two hydrocarbons covalently linked by an oxygen.

The term "alkylthio" refers to an alkyl group, as defined above, having a sulfur atom attached thereto. In some embodiments, the "alkylthio" moiety is represented by one of —S-alkyl, —S-alkenyl, and —S-alkynyl. Representative alkylthio groups include methylthio and ethylthio.

The term "amido" is art-recognized as an amino substituted by a carbonyl group.

The term "aralkyl", as used herein, refers to an alkyl group substituted with an aryl group. The term "heteroaralkyl", as used herein, refers to an alkyl group substituted with a heteroaryl group.

The term "heteroatom" as used herein means an atom of any element other than carbon or hydrogen. Examplary heteroatoms are nitrogen, oxygen, and sulfur.

As used herein, the term "thiol" means —SH; the term "hydroxyl" means —OH; and the term "sulfonyl" means —SO$_2$—.

As used herein the term "oxo" refers to a carbonyl oxygen atom.

As used herein, the term "alkaloid" refers to a naturally occurring organic compound containing at least one non-peptidic nitrogen atom.

"Microparticle", as used herein, generally refers to a particle having a diameter, such as an average diameter, from about 1 micron to about 100 microns, about 1 to about 50 microns, about 1 to about 30 microns, or about 1 micron to about 10 microns. The microparticles can have any shape. Microparticles having a spherical shape are generally referred to as "microspheres".

"Nanoparticle," as used herein, generally refers to a particle of any shape having an average diameter from about 1 nm up to, but not including, about 1 micron, about 5 nm to about 500 nm, or about 5 nm to about 300 nm. In some embodiments, the particles have an average diameter from about 100 nm to about 300 nm, about 100 nm to about 250 nm, or about 100 nm to about 200 nm. Nanoparticles having a spherical shape are generally referred to as "nanospheres".

"Mean particle size," as used herein, generally refers to the statistical mean particle size (diameter) of the particles in a population of particles. The diameter of an essentially spherical particle may be referred to as the physical or hydrodynamic diameter. The diameter of a non-spherical particle may refer preferentially to the hydrodynamic diameter. As used herein, the diameter of a non-spherical particle may refer to the largest linear distance between two points on the surface of the particle. Mean particle size can be measured using methods known in the art, such as dynamic light scattering.

"Monodisperse" and "homogeneous size distribution," are used interchangeably herein and describe a plurality of liposomal nanoparticles or microparticles where the particles have the same or nearly the same diameter or aerodynamic diameter. As used herein, a monodisperse distribution refers to particle distributions in which 75, 76, 77, 78, 79, 80, 81, 82, 83, 84, 85, 86, 86, 88, 89, 90, 91, 92, 93, 94, 95% or greater of the distribution lies within 85, 80, 75, 70, 65, 60, 55, 50, 45, 40, 35, 30, 25, 20, 15, or 10% of the mass median diameter or aerodynamic diameter.

EXAMPLES

The following examples are intended to illustrate certain embodiments of the present invention, but do not exemplify the full scope of the invention.

Example 1. Synthesis

The following example demonstrates the synthesis of polymer networks, as described herein.

A mixture of diol-PCL triol-PCL, hexamethylene diisocyanate and
unreactive PCL were blended at 70° C. and poured into Polydimethylsiloxane (PDMS) mold. The mold was then placed into an oven at 64° C. for 24 hours. The slightly lower temperature for curing was to minimize evaporation of hexamethylene diisocyanate, which generally resulted in the formation of bubbles in the polymer matrices. Non-crosslinked PCL formed crystal domains at temperatures below its melting temperature ($T_m$), and formed a physical cross-linking network. Cross-linked PCL formed a covalent network, which was generally not affected by temperature changes. The presence of crystalline domains generally has significant effects on mechanical properties of the polymer. Upon heating to the melting point of the crystalline domains, the physical network switches off and the previous force equilibrium breaks, therefore the macroscopic shape was primarily determined by the shape of covalent network, thus performing shape transformation.

The PCL based shape memory polymers are labeled using form of DaTbLc.d (a, b, c and d are actual numbers), e.g. D3T1L45k.4, in which, D, T and L are short forms of diol-PCL, triol-PCL and non-crosslinked PCL, D3T1 means dio-PCL and triol-PCL are reacted in a hydroxyl group ratio of 3 to 1, L45k.4 refers to non-crosslinked PLC with number mean molecular weight (Mn) of 45 kDalton is used, which made up 40% of total mass. Hexamethylene diisocyanate was added according to 1.05 NCO group (5% excess to compensate for evaporation during reaction) per hydroxyl group in triol-PCL and diol-PCL for all formulations.

Example 2. Materials Characterization

The following example illustrates the mechanical properties of the polymer network materials, as described herein.

Figure 3:
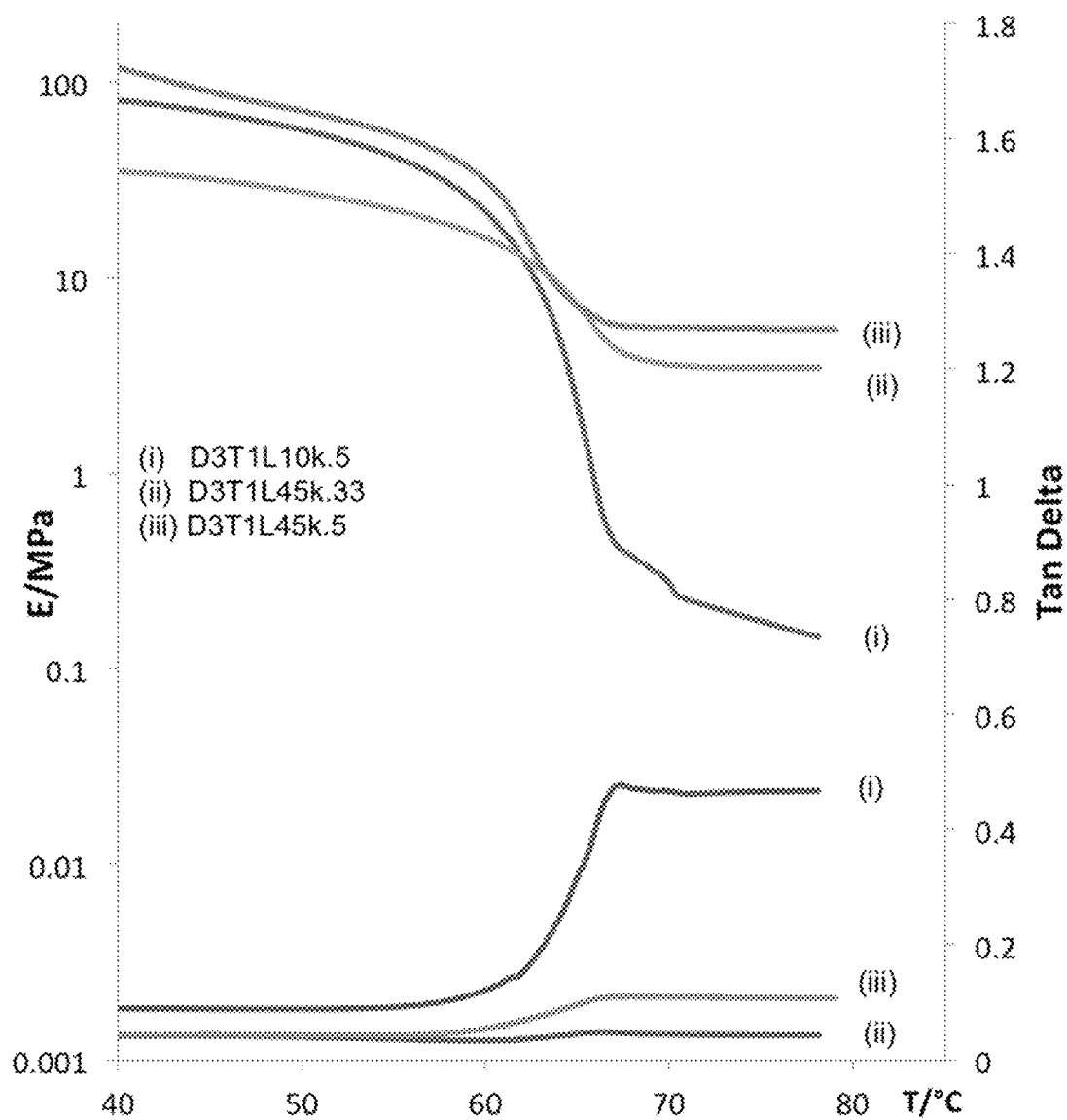
FIG. 3 is a plot of the dynamic mechanical analysis showing the Young's modulus and tan delta versus temperature for (i) D3T1L10k.5, (ii) D3T1L45k.33, (iii) D3T1L45k.5, according to one set of embodiments.

To find out the relationship between the composition and the mechanical and thermal properties, Dynamic Mechanical Analysis (DMA) was performed as shown in FIG. 3. FIG. 3 shows the softening temperature, energy dissipation (tan delta) and mechanical properties below and above the softening temperature. The tan delta graph shows an increase from one plateau to another, indicating that the transformation is a crystalline structure melting. By comparing the elastic modulus, which can be tuned by adjusting the mass ratio and mean molecular weight of non-crosslinked PCL.

A correlation between the percentage of non-crosslinked molecules added and the elastic modulus of the polymer blend from the elastic modulus against temperature reading measured was observed. FIG. 3 shows the mass ratio of non-crosslinked PCL effects on both softening temperatures and elastic modulus, e.g. as mass ratio of non-crosslinked PCL increased from 33% in D3T1L145k.33 to 50% in D3T1L45k.5, elastic modulus increased from 34.9 to 114.7 MPa at 40° C., while the softening temperature decreased from 67 to 62° C. The DMA results also showed that by changing the molecular weight form 10 kDalton to 45 kDalton, the elastic modulus increased from 75.6 to 114.7 MPa at 40° C., and the softening temperature increased for 2° C. Also, the tan delta against temperature diagram shows the increase from one plateau to another plateau. These data suggest that the nature of transformation was via a crystalline structure melt, and that modulation of thermal and mechanical properties of cross-linked PCL can be achieved by tuning their compositions. The mechanical properties of the materials were not observed to change significantly below their softening temperature.

Figure 4A:
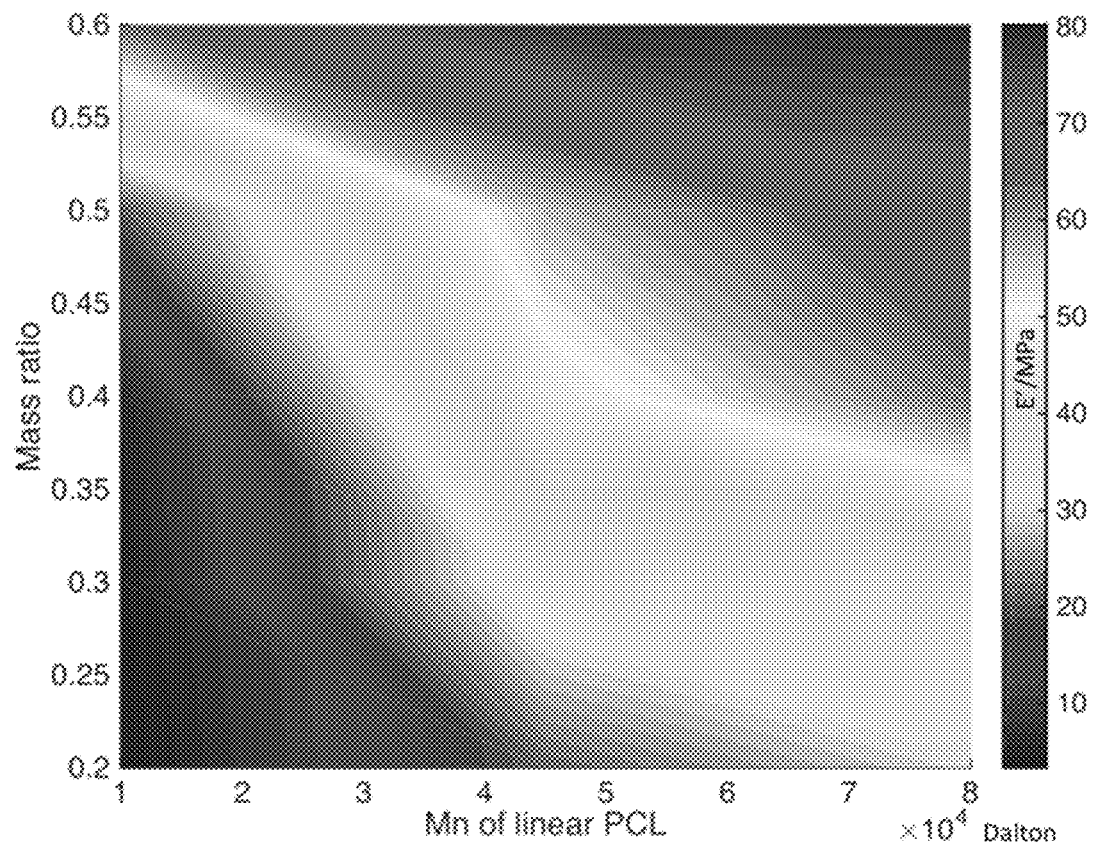
FIG. 4A is a plot of elastic modulus at room temperature versus mass ratio and mean number molecular weight of non-crosslinked PCL, according to one set of embodiments.
Figure 4B:
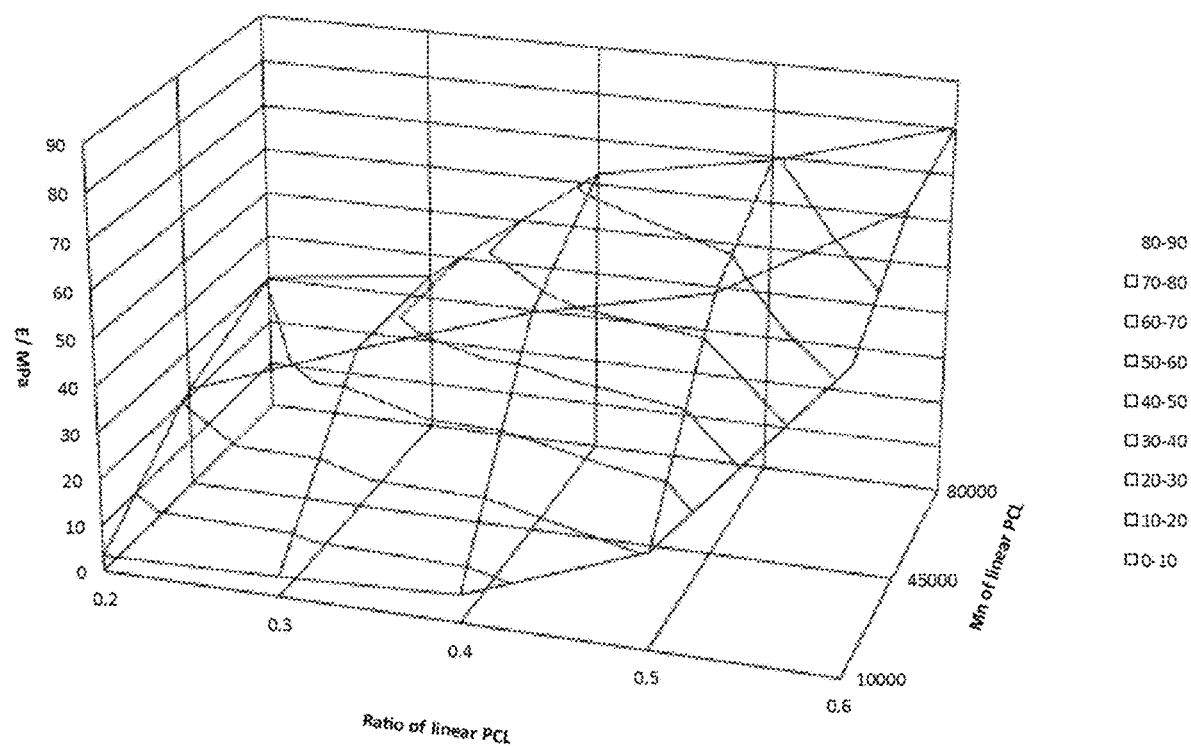
FIG. 4B is a wireframe plot of the plot of elastic modulus at room temperature versus mass ratio and mean number molecular weight of non-crosslinked PCL in FIG. 4A, according to one set of embodiments.
Figure 4C:
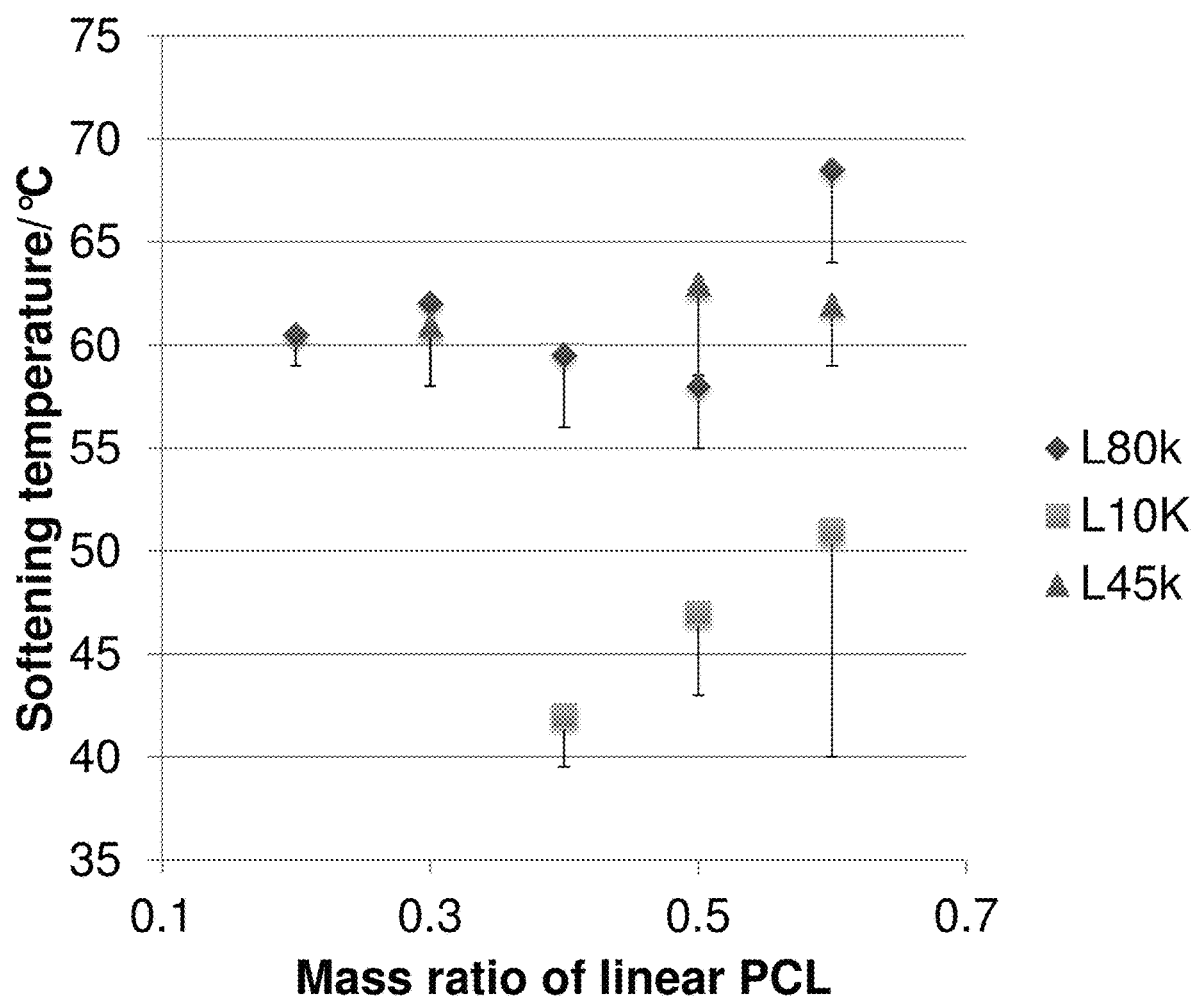
FIG. 4C is a plot of softening temperature versus mass ratio of non-crosslinked PCL for various polymer networks, according to one set of embodiments.

FIG. 4A summarizes results of the elastic modulus of 15 different formulations, which extrapolate into a counter map which may enable predictions of mechanical behavior of different formulations. FIG. 4B is a wireframe plot of the plot of elastic modulus at room temperature versus mass ratio and mean number molecular weight of non-crosslinked PCL shown in FIG. 4A FIG. 4C shows a plot of softening temperature versus mass ratio for 3 different formulations.

Example 3. Shape Recovery

Additional polymer networks were synthesized as described in Example 1 and summarized in Table 1, below. The following example illustrates the shape recovery (strain recovery) of these polymer networks.

Figure 5A:
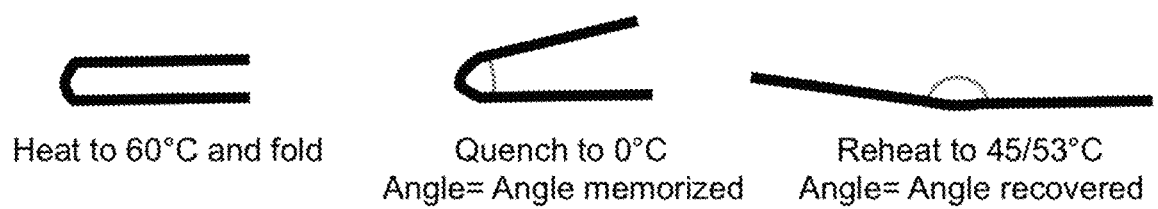
FIG. 5A is a schematic of a shape memory process, according to one set of embodiments.

One material specific parameter is the strain recovery, which characterizes the shape memory polymer's ability to recover its shape after being thermally triggered. As shown in FIG. 5A, a flat testing piece was heated to 60° C. and folded, the memorized angle was recorded after quenching it to 0° C., and recovery angle was measured from the material at specific temperature. Shape recovery ratio is defined by the equation:

shape recovery=1−((angle memorized)/(angle recovered)).

As shown in Table 1, it is shown that compositions, such as D3T1L10k.6, D3T1L0k.4 and D3T1L45k.4, achieve complete transformation in the temperature range of 45 to 53° C. (0 at 45° C. and 1.0 at 53° C.). For safety considerations, the device, in some cases, may effectively achieve transformation below 53° C. The onset temperature of shape recovery may be tuned above 45° C. to prevent unintentional triggering of transformation property due to, for example, intake of hot food or liquid. Therefore, a series of materials including D3T1L10k.6, D3T1L45k.3, D3T1L45k.4, D3T1L80k.2, D1T1L10k.4, have been found to perform novel shape memory at a safe temperature range.

TABLE 1

| Composition | Shape Recovery at 45° C. | Shape Recovery at 53° C. |
|---|---|---|
| D3T1L10k.2 | 0 | 0 |
| D3T1L10k.3 | 0.5 | 0.5 |
| D3T1L10k.4 | 0.7 | 0.7 |
| D3T1L10k.5 | 0.8 | 0.8 |
| D3T1L10k.6 | 0 | 1 |
| D3T1L45k.2 | 0.5 | 1 |
| D3T1L45k.3 | 0.1 | 0.9 |
| D3T1L45k.4 | 0 | 0.9 |
| D3T1L45k.5 | 0.7 | 1 |
| D3T1L45k.6 | 1 | 1 |
| D3T1L80k.2 | 0 | 0.8 |
| D3T1L80k.3 | 0.2 | 0.5 |
| D3T1L80k.4 | 0.1 | 0.5 |
| D3T1L80k.5 | 0 | 0.4 |
| D3T1L80k.6 | 0 | 0.5 |
| D6T1L10k.4 | 0.1 | 0.6 |
| D1T1L10k.4 | 0 | 1 |
| D1T3L10k.4 | 0.7 | 1 |
| D1T6L10k.4 | 0.5 | 0.7 |

Figure 5B:
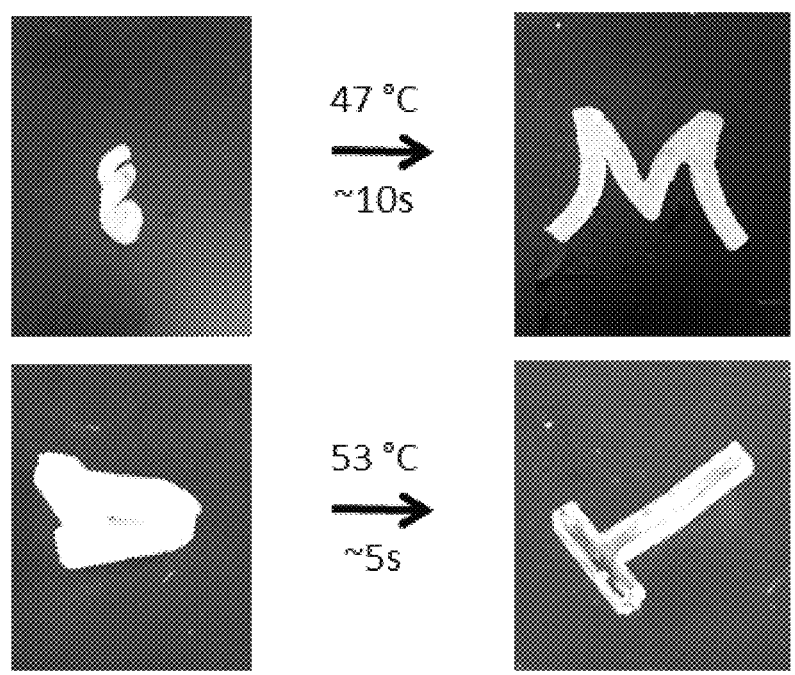
FIG. 5B are photograms of polymer networks undergoing a shape recovery process at the times and temperatures indicated, according to one set of embodiments.

FIG. 5B shows additional examples of polymer networks undergoing shape recovery above their respective softening temperatures (about 47° C. and about 53° C., as indicated). On the left, the picture shows programmed polymer networks in their temporary shapes. After incubated in a water bath at the indicated temperatures, they recover to their as cast shapes, which are M and T shapes.

Example 4. Biocompatibility/Cytotoxicity

The following example demonstrates the biocompatibility/cytotoxicity of the polymer networks, described in Examples 1-3.

Figure 6A:
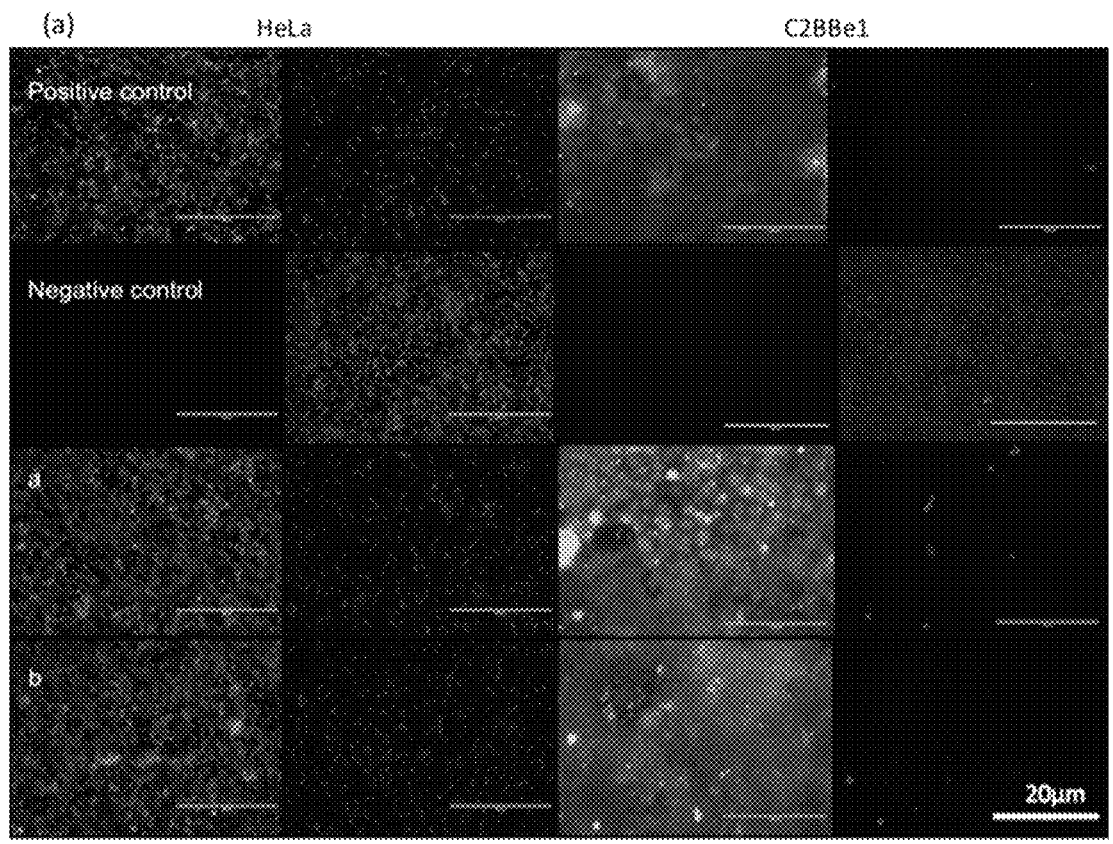
FIG. 6A are microscopy images of 20 mm$^3$ of samples of D3T1L10k.5 and D3T1L45k.4 incubated individually in 10 ml of SGF at 36.5° C. for 10 days. The SGF was then neutralized by NaOH solution. HeLa and Caco-2 cell lines are incubated in the neutralized SGF to test cytotoxicity, according to one set of embodiments.
Figure 6B:
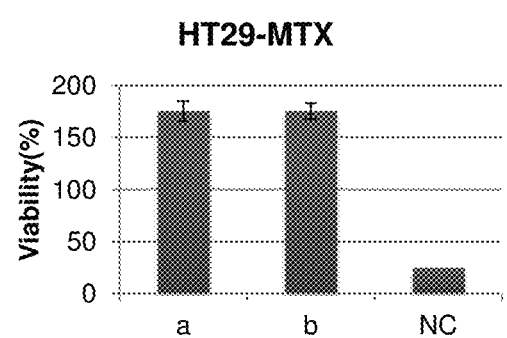
FIGS. 6B-6E are cells viability plots using almarBlue® staining, according to one set of embodiments.
Figure 6C:
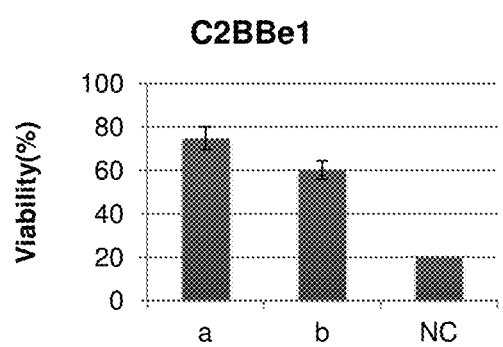
Figure 6D:
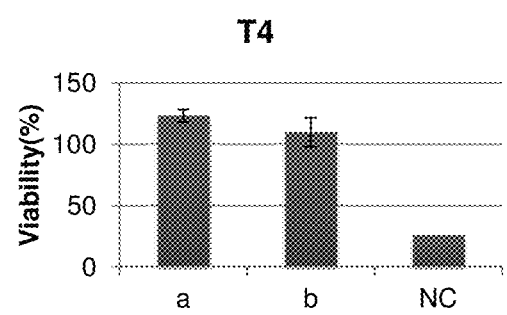
Figure 6E:
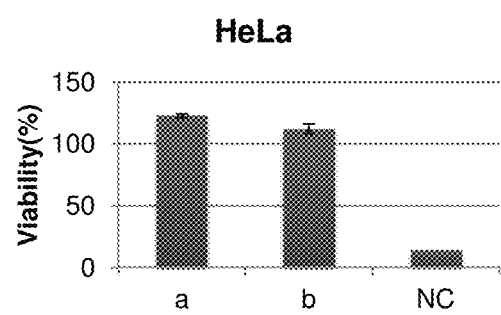

Cytotoxicity of the materials was tested using 4 cell lines: HT29-MTX C2BBe1, T4, Hela. According to ISO 10993-1: standard for testing implants which have surface contact with mucosal membrane for 24 hours to 30 days, the material should not release cytotoxic substances. PCL based SMP samples were submerged in simulated gastric fluid (SGF) at 37° C. under stirring to simulate gastric environment under constant motion. After 10 days the SGF was neutralized with sodium hydroxide to pH 7.0 before being added to cell culture medium at one-to-one ratio. Volume ratio between the testing material and the neutralized SGF that the material was submerged in was 1:1000. Cell culture medium was prepared by mixing DMEM, 10% FBS, 1% of penicillin and streptomycin antibiotics and 1% of non-essential amino acids. The cells were incubated with the cell culture medium-neutralized mixture for 10 days. A positive control was obtained by incubating the cells with cell culture medium only. A negative control was obtained by incubating the cells with 70% ethanol for 30 minutes. FIG. 6A shows a qualitative live/dead assay shows that cellular viability did not affect the medium containing cross-linked PCL. Almar-Blue® reagent was added to the cell lines, which stained living cells with a fluorescent dye enabling fluorescent quantitation of viability. Results of the cell count were plotted in viability plots as shown in FIGS. 6B-6E. PCL based SMP samples generally demonstrated a significantly higher viability than the negative control.

Example 5. Induction of Shape Memory

Remotely triggered shape memory was obtained by embedding micron size paramagnetic particles (including irons and iron oxides particles of various geometries) into PCL based polymer networks, which formed a Magnetic sensitive Shape Memory Composite (MSMC). Radio waves can be used to trigger the shape memory and can generally safely penetrate human body. The temperatures generated by induction was localized, such that the surface in contact with human body was kept within a safe temperature range.

Figure 7:
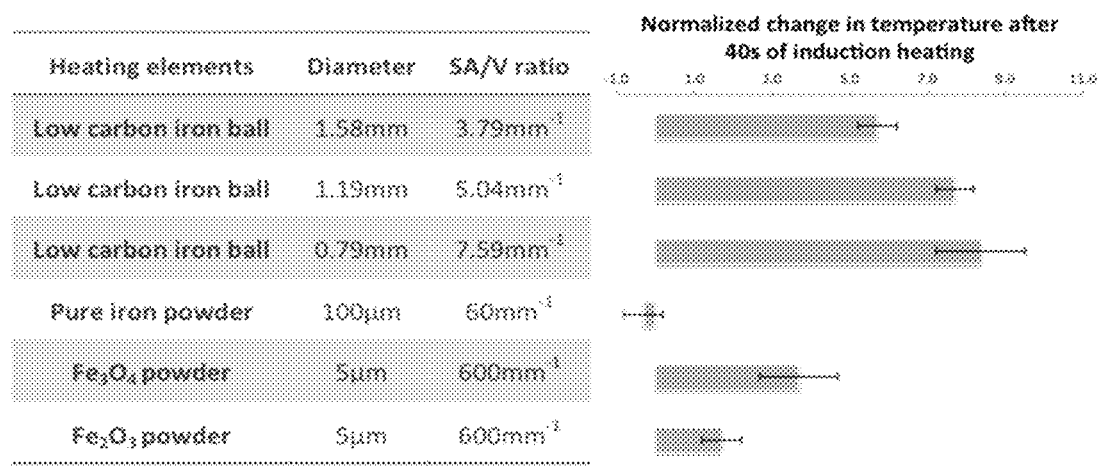
FIG. 7 is a plot of normalized change in temperature after 40 seconds of induction heating, according to one set of embodiments.

Various paramagnetic particles were tested as shown in FIG. 7. Normalized temperature change was obtained by comparing the temperature of the region around the embedded paramagnetic particles 40 seconds after switching the induction heater. Iron balls, e.g. 0=0.79 mm, with large surface to volume ratio, were found to be most effective in heating the materials than other particles.

Figure 8:
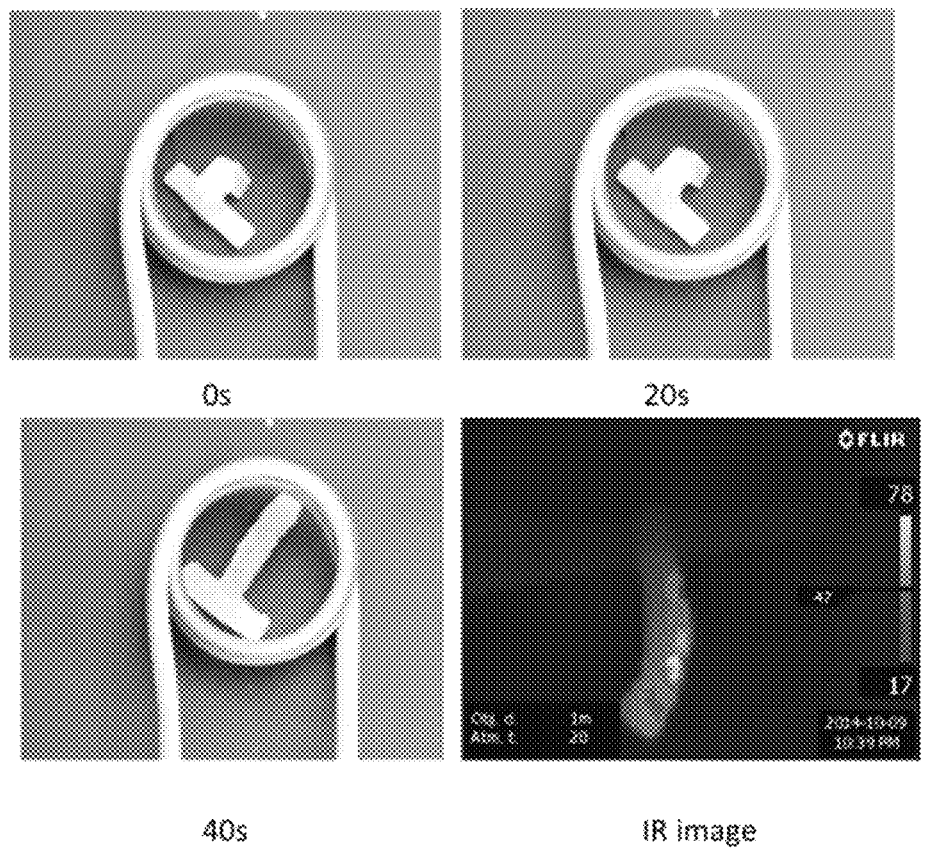
FIG. 8 shows a polymer network made from D3T1L45k.4 with shape recovery in 40s under 2 MHz, 5 kAm-1 alternating magnetic field. An IR image obtained by an infrared pyrometer shows sufficient heat has been evolved from the magnetic particles, according to one set of embodiments.

FIG. 8 shows a series of images of shape recovery from a bended T shape back to its original shape by induction heating with a radio-frequency induction heater which generated a 2 MHz, 5 kAm$^{-1}$ alternating magnetic field. The infrared image shows that only materials directly adjacent the iron particles were heated up (up to 78° C.) while the materials on the surface stayed relatively cool (below 47° C.).

Figure 9A:
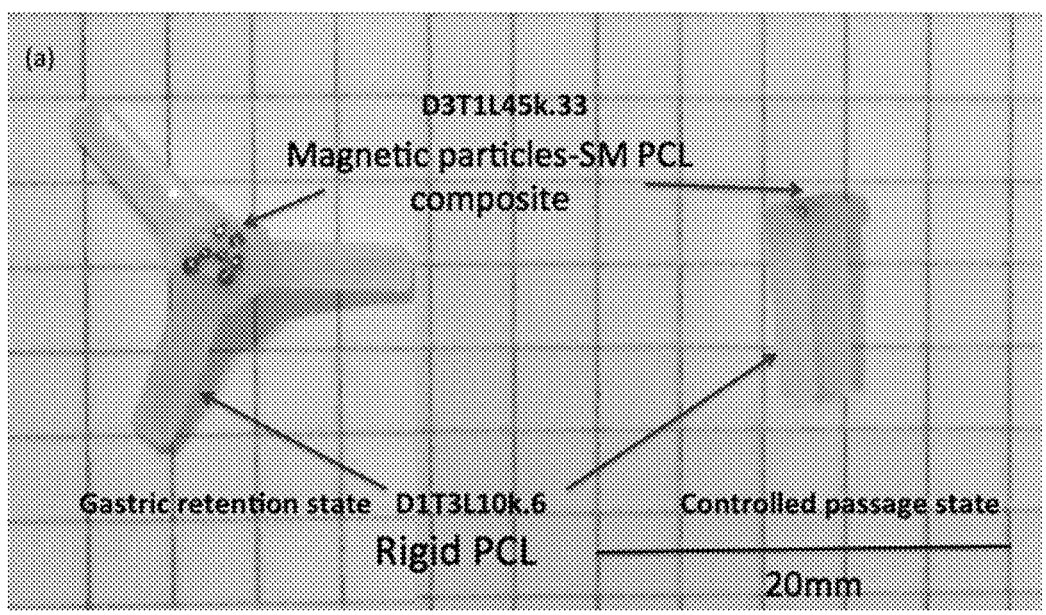
FIG. 9A shows a gastric retention device capable of being packed into a size-4-gelatin capsule, according to one set of embodiments.
Figure 9B:
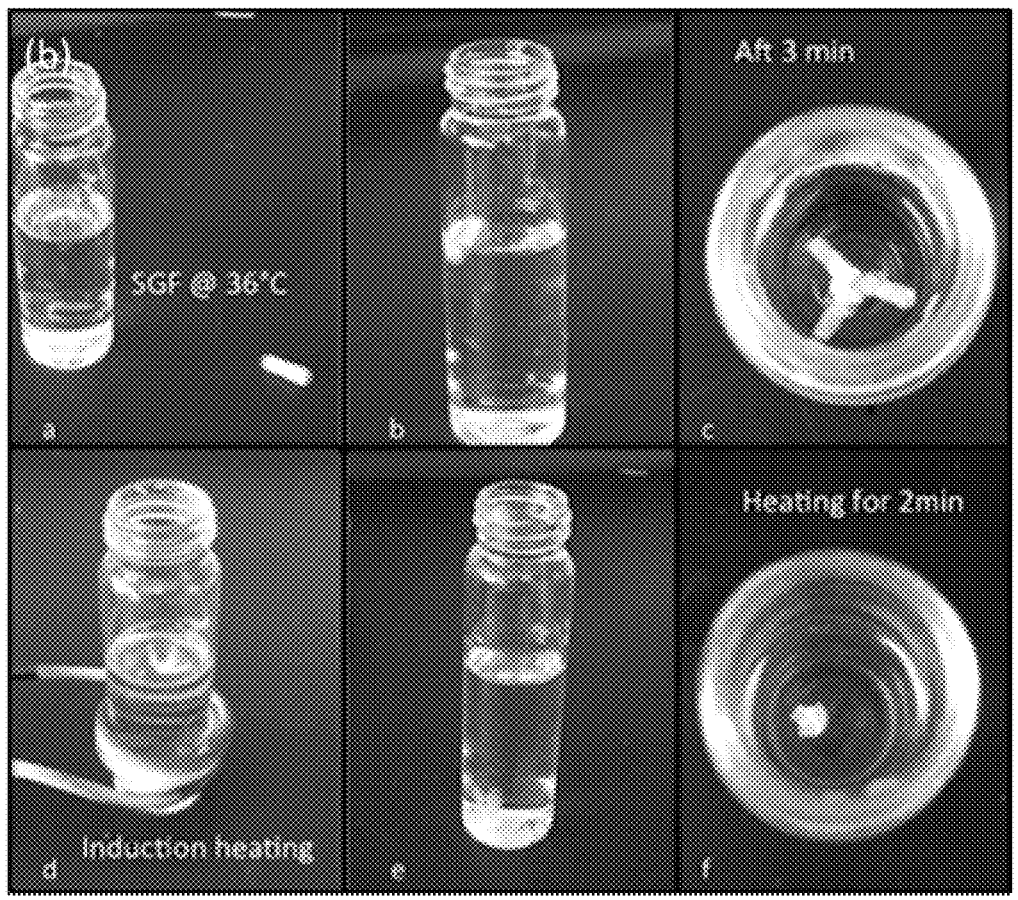
FIG. 9B shows the dissolution and stimulation of shape memory of the device in FIG. 9A, according to one set of embodiments.

FIG. 9 shows a prototype retention device made with cross-linked PCL and MSMC as denoted in the picture. This prototype was designed based on performing gastric retention in rats. The device was folded in to a standard size 4 capsule and deployed in simulated gastric fluid under 36° C. to simulate the escaping from the capsule in animal stomach and restoring its original shape for the gastric retention. Upon induction heating for 2 minutes, the device's largest cross-sectional dimension decreased from 20 mm to 4 mm, which would be sufficiently small to initiate the passage of the device from the stomach when this device would be deployed in a rat's stomach.

Example 6. Manufacture of Prototype Device

Figure 10A:
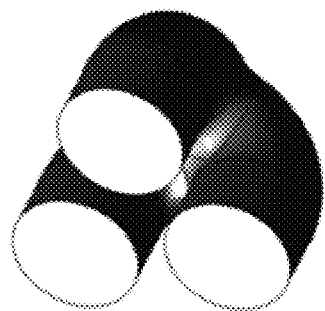
FIG. 10A shows a schematic of a positive mold of an exemplary shape memory device, according to one set of embodiments.
Figure 10B:
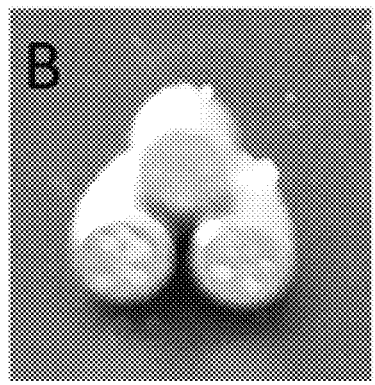
FIG. 10B is a photograph of a positive mold of an exemplary shape memory device, according to one set of embodiments.
Figure 10C:
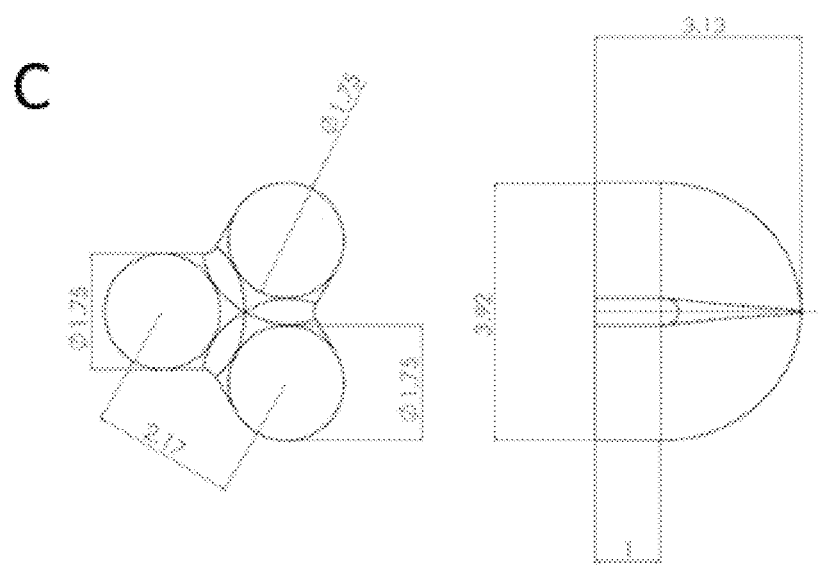
FIG. 10C is a schematic diagram of a positive mold of an exemplary shape memory device, according to one set of embodiments.
Figure 10D:
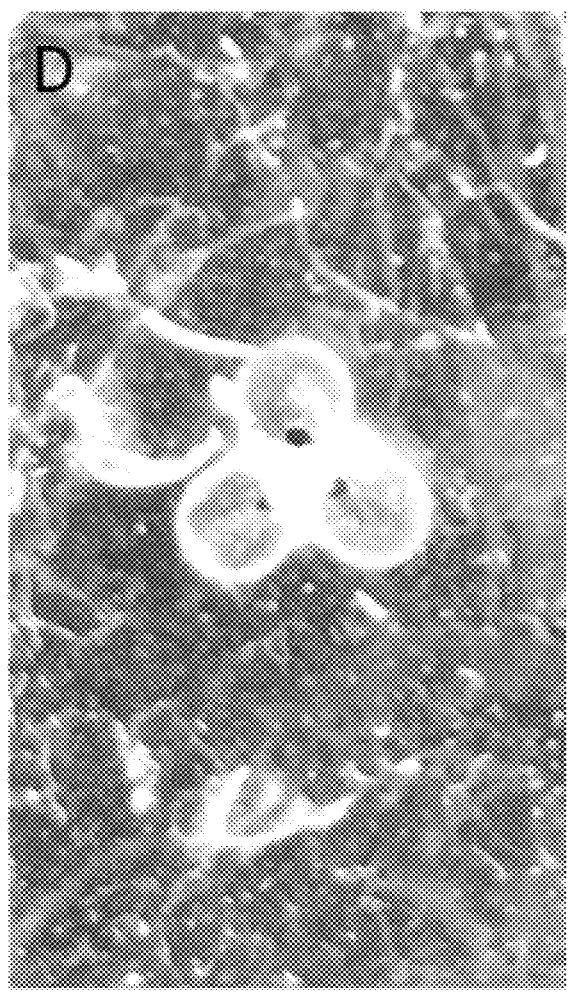
FIG. 10D is a negative mold of an exemplary shape memory device produced using the positive mold in FIG. 10B, according to one set of embodiments.

FIGS. 10A-10D show a miniature prototype designed for a rat retention study. FIG. 10A is a schematic of the 3D shape of a designed three-arm-star shape, and is further detailed in FIG. 10C. FIG. 10B is a photograph of the 3D printed metal positive mold of the design shown in FIGS. 10A and 10C. The three-arm-star shape retention device was designed to be folded and fitted into the size 5 capsule for oral delivery of encapsulated device into, for example, rats. FIG. 10D shows the negative PDMS mold is made using the positive mold (FIG. 10B), and could, for example, be used to fabricate at least a portion of a retention device.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Any terms as used herein related to shape, orientation, alignment, and/or geometric relationship of or between, for example, one or more articles, structures, forces, fields, flows, directions/trajectories, and/or subcomponents thereof and/or combinations thereof and/or any other tangible or intangible elements not listed above amenable to characterization by such terms, unless otherwise defined or indicated, shall be understood to not require absolute conformance to a mathematical definition of such term, but, rather, shall be understood to indicate conformance to the mathematical definition of such term to the extent possible for the subject matter so characterized as would be understood by one skilled in the art most closely related to such subject matter. Examples of such terms related to shape, orientation, and/or geometric relationship include, but are not limited to terms descriptive of: shape—such as, round, square, circular/circle, rectangular/rectangle, triangular/triangle, cylindrical/cylinder, elipitical/ellipse, (n)polygonal/(n)polygon, etc.; angular orientation—such as perpendicular, orthogonal, parallel, vertical, horizontal, collinear, etc.; contour and/or trajectory—such as, plane/planar, coplanar, hemispherical, semi-hemispherical, line/linear, hyperbolic, parabolic, flat, curved, straight, arcuate, sinusoidal, tangent/tangential, etc.; direction—such as, north, south, east, west, etc.; surface and/or bulk material properties and/or spatial/temporal resolution and/or distribution—such as, smooth, reflective, transparent, clear, opaque, rigid, impermeable, uniform(ly), inert, non-wettable, insoluble, steady, invariant, constant, homogeneous, etc.; as well as many others that would be apparent to those skilled in the relevant arts. As one example, a fabricated article that would described herein as being "square" would not require such article to have faces or sides that are perfectly planar or linear and that intersect at angles of exactly 90 degrees (indeed, such an article can only exist as a mathematical abstraction), but rather, the shape of such article should be interpreted as approximating a "square," as defined mathematically, to an extent typically achievable and achieved for the recited fabrication technique as would be understood by those skilled in the art or as specifically described. As another example, two or more fabricated articles that would described herein as being "aligned" would not require such articles to have faces or sides that are perfectly aligned (indeed, such an article can only exist as a mathematical abstraction), but rather, the arrangement of such articles should be interpreted as approximating "aligned," as defined mathematically, to an extent typically achievable and achieved for the recited fabrication technique as would be understood by those skilled in the art or as specifically described.

What is claimed:

1. A method for removing a device from a location internally of a subject, comprising:
   stimulating the device such that the device obtains a second configuration, wherein the second configuration is sufficiently small such that the device is removed from the location internally of the subject;
   wherein the device has a first configuration different than the second configuration prior to stimulating;
   wherein the second configuration has a largest cross-sectional dimension at least about 10% less than a largest cross-sectional dimension of the first configuration, and/or
   wherein the second configuration has a convex hull at least about 10% less than a convex hull of the first configuration;
   wherein the device comprises a triggerable shape memory composition, the triggerable shape memory composition comprising:
      a polymer network comprising a first polymeric material and a second polymeric material; and
      a plurality of paramagnetic particles associated with the polymer network;
   wherein the first polymeric material is a non-crosslinked polymer having a softening temperature of greater than or equal to about 45° C.;
   wherein the second polymeric material is a crosslinked polymer;
   wherein the polymer network is constructed and arranged to have a first configuration below the softening temperature of the first polymeric material and a second configuration different than the first configuration above the softening temperature of the first polymeric material; and
   wherein the second configuration has a largest cross-sectional dimension at least about 10% less than a largest cross-sectional dimension of the first configuration and/or
   wherein the second configuration has a convex hull at least about 10% less than a convex hull of the first configuration.

2. A method for selectively retaining a device in a location internally of a subject, comprising:
   administering the device, wherein the device has a first configuration, wherein the device obtains a second configuration in the location internally of the subject such that the device is retained within the location;
   stimulating, after a period of time, the device such that the device obtains the first configuration, wherein the first configuration is such that device is removed from the location;
   wherein the device comprises a triggerable shape memory composition, the triggerable shape memory composition comprising:
      a polymer network comprising a first polymeric material and a second polymeric material; and
      a plurality of paramagnetic particles associated with the polymer network;
   wherein the first polymeric material is a non-crosslinked polymer having a softening temperature of greater than or equal to about 45° C.;
   wherein the second polymeric material is a crosslinked polymer;
   wherein the polymer network is constructed and arranged to have a first configuration below the softening temperature of the first polymeric material and a second configuration different than the first configuration above the softening temperature of the first polymeric material; and
   wherein the second configuration has a largest cross-sectional dimension at least about 10% less than a largest cross-sectional dimension of the first configuration and/or
   wherein the second configuration has a convex hull at least about 10% less than a convex hull of the first configuration.

3. A method as in claim 2, wherein the device is administered orally.

4. A method as in claim 2, wherein the device is contained within a capsule prior to and/or during administering the device.

5. A method as in claim 2, wherein stimulating the device comprises applying an external signal to the subject.

6. A method as in claim 2, wherein stimulating the device comprises heating the device.

7. A method as in claim 2, wherein stimulating the device comprises induction.

8. A method as in claim 2, wherein the device is heated to a temperature ranging between 45° C. and 65° C., inclusive.

9. A method as in claim 2, wherein the device comprises a polymer network having a softening temperature ranging between 45° C. and 65° C., inclusive.

10. A triggerable retention device for controlled retention internally of a subject, comprising:
    an expanded profile in which the device, when positioned at a location internally of the subject, is retained at that location, the device being susceptible to a stimulus applied from externally of the subject whereby the device assumes a contracted profile and is eliminated from the location internally of the subject,
    wherein the device comprises a triggerable shape memory composition, the triggerable shape memory composition comprising:
       a polymer network comprising a first polymeric material and a second polymeric material; and
       a plurality of paramagnetic particles associated with the polymer network;
    wherein the first polymeric material is a non-crosslinked polymer having a softening temperature of greater than or equal to about 45° C.;
    wherein the second polymeric material is a crosslinked polymer;
    wherein the polymer network is constructed and arranged to have a first configuration below the softening temperature of the first polymeric material and a second configuration different than the first configuration above the softening temperature of the first polymeric material; and
    wherein the second configuration has a largest cross-sectional dimension at least about 10% less than a largest cross-sectional dimension of the first configuration and/or
    wherein the second configuration has a convex hull at least about 10% less than a convex hull of the first configuration.

11. A device as in claim 10, wherein the first polymeric material and/or second polymeric material comprises polycaprolactone and/or polylactic acid.

12. A device as in claim 10, wherein the location internal of the subject is within the gastrointestinal tract.

13. A triggerable retention device as in claim 10, wherein the device comprises a triggerable shape memory composition, the triggerable shape memory composition comprising:
   a polymer network comprising a first polymeric material and a second polymeric material;
   a plurality of non-polymeric portions associated with the polymer network which, upon exposure to the external stimulus, facilitate heating of the first polymeric material to at least about 45° C.;
   wherein the first polymeric material has a softening temperature of greater than or equal to about 45° C.;
   wherein the polymer network is constructed and arranged to have a first configuration below the softening temperature of the first polymeric material and a second configuration different than the first configuration above the softening temperature of the first polymeric material; and
   wherein the second configuration has a largest cross-sectional dimension at least about 10% less than a largest cross-sectional dimension of the first configuration and/or
   wherein the second configuration has a convex hull at least about 10% less than a convex hull of the first configuration.

14. A triggerable retention device as in claim 10, wherein the plurality of non-polymeric portions comprise paramagnetic particles.

15. A triggerable retention device as in claim 10, wherein the softening temperature is a glass transition temperature of the first polymeric material.

16. A triggerable retention device as in claim 10, wherein the softening temperature is a melting temperature of the first polymeric material.

17. A triggerable retention device as in claim 10, wherein the second polymeric material has a softening temperature greater than the softening temperature of the first polymeric material.

18. A triggerable retention device as in claim 10, wherein the polymeric material comprises polycaprolactone and/or polylactic acid.

19. A triggerable retention device for controlled retention internally of a subject, comprising:
   an expanded profile in which the device, when positioned at a location internally of the subject, is retained at that location under normal physiological conditions, the device being susceptible to a stimulus applied from externally of the subject whereby the device assumes a contracted profile and is eliminated from the location internally of the subject,
   wherein the device comprises a triggerable shape memory composition, the triggerable shape memory composition comprising:
      a polymer network comprising a first polymeric material and a second polymeric material;
      a plurality of non-polymeric portions associated with the polymer network which, upon exposure to an external stimulus, facilitate heating of the first polymeric material to at least about 45° C.;
   wherein the first polymeric material has a softening temperature of greater than or equal to about 45° C.;
   wherein the polymer network is constructed and arranged to have a first configuration below the softening temperature of the first polymeric material and a second configuration different than the first configuration above the softening temperature of the first polymeric material; and
   wherein the second configuration has a largest cross-sectional dimension at least about 10% less than a largest cross-sectional dimension of the first configuration and/or
   wherein the second configuration has a convex hull at least about 10% less than a convex hull of the first configuration.

* * * * *